US012577235B2

(12) United States Patent
Gao et al.

(10) Patent No.: US 12,577,235 B2
(45) Date of Patent: Mar. 17, 2026

(54) CRYSTALLINE FORM OF CXCR2 ANTAGONIST AND APPLICATION THEREOF

(71) Applicant: Shenzhen Optimum Biological Technology Co., Ltd, Guangdong (CN)

(72) Inventors: Feng Gao, Shanghai (CN); Yuan Chen, Shanghai (CN); Peng Zhang, Shanghai (CN); Yunfu Luo, Shanghai (CN)

(73) Assignee: SHENZHEN OPTIMUM BIOLOGICAL TECHNOLOGY CO., LTD, Shenzhen (CN)

( * ) Notice: Subject to any disclaimer, the term of this patent is extended or adjusted under 35 U.S.C. 154(b) by 1103 days.

(21) Appl. No.: 17/597,563

(22) PCT Filed: Jul. 10, 2020

(86) PCT No.: PCT/CN2020/101352
§ 371 (c)(1),
(2) Date: Jul. 5, 2022

(87) PCT Pub. No.: WO2021/004531
PCT Pub. Date: Jan. 14, 2021

(65) Prior Publication Data

US 2022/0340549 A1 Oct. 27, 2022

(30) Foreign Application Priority Data

Jul. 11, 2019 (CN) ......................... 201910626168.6

(51) Int. Cl.
*C07D 405/12* (2006.01)
*C07C 233/83* (2006.01)
*A61P 11/00* (2006.01)
*C07C 57/145* (2006.01)

(52) U.S. Cl.
CPC ........ *C07D 405/12* (2013.01); *C07B 2200/13* (2013.01)

(58) Field of Classification Search
CPC . C07D 405/12; C07B 2200/13; C07C 57/145; C07C 233/83; A61P 11/00
See application file for complete search history.

(56) References Cited

U.S. PATENT DOCUMENTS 11,136,315 B2 * 10/2021 Chen .................. C07D 491/048

FOREIGN PATENT DOCUMENTS

| | | | |
|---|---|---|---|
| CN | 1424910 | A | 6/2003 |
| CN | 101472477 | A | 7/2009 |
| CN | 101495113 | A | 7/2009 |
| CN | 106660950 | A | 5/2017 |
| CN | 107027306 | A | 8/2017 |
| WO | 2004039775 | A2 | 5/2004 |
| WO | 2007124424 | A2 | 4/2007 |
| WO | 2017156270 | A1 | 9/2017 |
| WO | 2019137484 | A1 | 7/2019 |

OTHER PUBLICATIONS

Kirsten et al. The safety and tolerability of oral AZD5069, a selective CXCR2 antagonist, in patients with moderate-to-severe COPD, Pulmonary Pharmacology & Therapeutics, 2015, 36-41 (Year: 2015).*

* cited by examiner

*Primary Examiner* — Bruck Kifle
*Assistant Examiner* — Kevin S Martin
(74) *Attorney, Agent, or Firm* — NKL Law; Allen Xue

(57) ABSTRACT

A crystalline form of CXCR2 antagonist, such as Compound 1, is used in preparing a drug for treating CXCR2-related diseases.

Compound 1

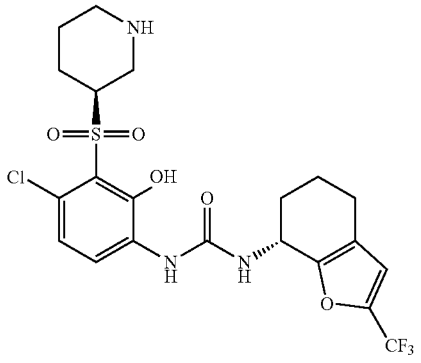

5 Claims, 27 Drawing Sheets

CRYSTALLINE FORM OF CXCR2 ANTAGONIST AND APPLICATION THEREOF

CROSS-REFERENCE TO RELATED APPLICATIONS

This application is a U.S. national stage entry of PCT International Application No. PCT/CN2020/101352, filed on Jul. 10, 2020, which claims priority to Chinese Patent Application No. CN201910626168.6, filed on Jul. 11, 2019, the content of which is incorporated herein by reference in its entirety.

TECHNICAL FIELD

The present disclosure relates to a crystalline form of a CXCR2 antagonist and use thereof in preparing a medicament for treating CXCR2 related diseases.

BACKGROUND

Chronic obstructive pulmonary disease (COPD) is a debilitating disease characterized by progressive airflow limitation caused by chronic airway inflammation. It is usually caused by inhalation of harmful particles and gases, which are mainly from smoking and air pollution. Its symptoms include mucus hypersecretion, narrowed airway, fibrosis and loss of alveoli. It leads to average weight loss, osteoporosis, cardiovascular diseases and psychological damage. Current treatments for moderate to severe chronic obstructive pulmonary disease are relatively ineffective and no available drugs can significantly retard disease progression or death. Global Initiative for Chronic Obstructive Lung Disease (GOLD) recommends long-acting bronchodilators (long-acting muscarinic antagonists or LABAs, and long-acting beta-agonists or LAMAs) as first-line maintenance therapy for patients with moderate to severe COPD. Although such drugs can produce effective bronchodilation, they do not treat the underlying inflammation in patients with chronic obstructive pulmonary disease. Inhaled corticosteroids (ICSs), while somewhat effective in patients with asthma, are largely ineffective on chronic obstructive pulmonary disease. Therefore, when bronchodilators are ineffective in patients, additional therapies, including inhaled corticosteroids (ICSs), can only be used with caution.

COPD is a chronic inflammatory disease, suggesting that effective anti-inflammatory therapy is the largest unmet therapeutic need in the current field of chronic obstructive pulmonary disease. Roflumilast is an oral phosphodiesterase 4 (PDE4) inhibitor, and is the first approved oral anti-inflammatory drug for the treatment of chronic obstructive pulmonary disease. However, use of roflumilast is limited by its strong side effects, and thus it is still necessary to develop other novel anti-inflammatory targets for treating chronic obstructive pulmonary disease.

Interleukin 8 (IL-8 or CXCL8) is a protein with 72 amino acid residues. It is a key factor in controlling recruitment and transferring of leukocytes at sites of inflammation. Interleukin 8 acts by binding to its receptor, a G protein-coupled receptor, which belongs to CXC chemokine receptors and includes CXCR1 and CXCR2. CXCR2 is highly expressed on the surface of human neutrophils. When interleukin 8 binds to CXCR2 on the surface of neutrophils, it causes a series of reactions in the cells, including calcium flux changes, degranulation and subsequent chemotaxis. Increased levels of interleukin 8 in a plurality of inflammatory diseases, such as arthritis, asthma, chronic obstructive pulmonary disease, etc., suggest that blocking its interaction with its receptor would be beneficial to these diseases.

WO2007124424 discloses use of a CXCR2 antagonist Danirixin in treating related diseases.

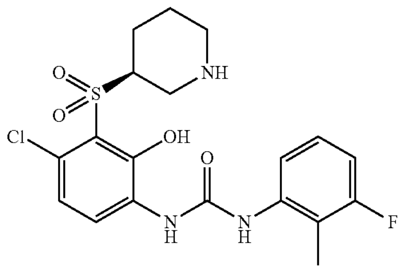

Danirixin

SUMMARY

The present disclosure provides a crystalline form A of a compound 1 having diffraction peaks in an X-ray powder diffraction pattern (XRPD) at the following 2-theta values: 4.02±0.20°, 15.95±0.20° and 18.59±0.20°.

Compound 1

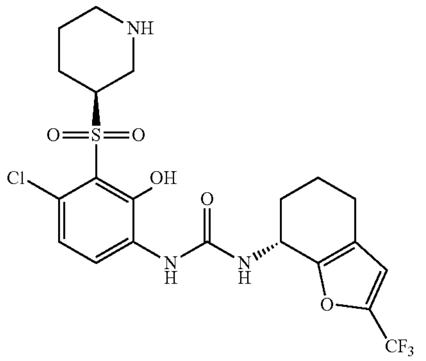

In some embodiments of the present disclosure, the crystalline form A of the compound 1 described above has diffraction peaks in an X-ray powder diffraction pattern at the following 2-theta values: 4.02±0.20°, 14.54±0.20°, 15.95±0.20°, 16.56±0.20°, 17.14±0.20°, 18.59±0.20°, 19.98±0.20° and 20.67±0.20°.

In some embodiments of the present disclosure, the crystalline form A of the compound 1 described above has diffraction peaks in an X-ray powder diffraction pattern at the following 2-theta values: 4.02°, 8.14°, 9.38°, 12.37°, 14.54°, 15.95°, 16.56°, 17.14°, 17.64°, 18.59°, 18.83°, 19.31°, 19.98°, 20.67°, 23.29°, 25.30° and 28.96°.

In some embodiments of the present disclosure, the crystalline form A of the compound 1 described above has an XRPD pattern as shown in FIG. 1.

In some embodiments of the present disclosure, the crystalline form A described above has XRPD pattern analysis data as shown in Table 1:

TABLE 1

XRPD pattern analysis data for the crystalline form A

| No. | 2-theta value (°) | Peak height (cts) | Interplanar spacing (Å) | Relative intensity (%) |
|---|---|---|---|---|
| 1 | 4.02 | 762.23 | 22.00 | 100.00 |
| 2 | 8.14 | 152.54 | 10.86 | 20.01 |
| 3 | 9.38 | 101.29 | 9.43 | 13.29 |
| 4 | 12.37 | 63.55 | 7.16 | 8.34 |
| 5 | 14.54 | 372.11 | 6.09 | 48.82 |
| 6 | 15.95 | 644.46 | 5.56 | 84.55 |
| 7 | 16.56 | 338.23 | 5.35 | 44.37 |
| 8 | 17.14 | 249.66 | 5.17 | 32.75 |
| 9 | 17.64 | 128.20 | 5.03 | 16.82 |
| 10 | 18.59 | 642.13 | 4.77 | 84.24 |
| 11 | 18.83 | 309.30 | 4.71 | 40.58 |
| 12 | 19.31 | 146.11 | 4.60 | 19.17 |
| 13 | 19.98 | 613.62 | 4.44 | 80.50 |
| 14 | 20.67 | 260.42 | 4.30 | 34.17 |
| 15 | 23.29 | 88.94 | 3.82 | 11.67 |
| 16 | 25.30 | 88.93 | 3.52 | 11.67 |
| 17 | 28.96 | 42.89 | 3.08 | 5.63 |

In some embodiments of the present disclosure, the crystalline form A described above has a differential scanning calorimetry (DSC) curve with a on-set point of an endothermic peak at 218.8±3° C.

In some embodiments of the present disclosure, the crystalline form A described above has a DSC pattern as shown in FIG. 2.

In some embodiments of the present disclosure, the crystalline form A described above has a thermogravimetric analysis (TGA) curve with a weight loss of up to 3.24% at 150.0±3° C.

In some embodiments of the present disclosure, the crystalline form A described above has a TGA pattern as shown in FIG. 3.

The present disclosure further provides a crystalline form B of the compound 1 having diffraction peaks in an X-ray powder diffraction pattern at the following 2-theta values: 7.88±0.20°, 8.69±0.20° and 16.45±0.20°.

In some embodiments of the present disclosure, the crystalline form B of the compound 1 described above has diffraction peaks in an X-ray powder diffraction pattern at the following 2-theta values: 7.88±0.20°, 8.69±0.20°, 11.37±0.20°, 12.47±0.20°, 15.32±0.20°, 16.45±0.20°, 17.49±0.20° and 22.90±0.20°.

In some embodiments of the present disclosure, the crystalline form B of the compound 1 described above has diffraction peaks in an X-ray powder diffraction pattern at the following 2-theta values: 7.88°, 8.69°, 11.37°, 12.47°, 15.32°, 16.45°, 17.49°, 20.04°, 21.24°, 22.90°, 23.71°, 24.14° and 24.90°.

In some embodiments of the present disclosure, the crystalline form B of the compound 1 described above has an XRPD pattern as shown in FIG. 4.

In some embodiments of the present disclosure, the crystalline form B described above has XRPD pattern analysis data as shown in Table 2:

TABLE 2

XRPD pattern analysis data for crystalline form B

| No. | 2-theta value (°) | Peak height (cts) | Interplanar spacing (Å) | Relative intensity (%) |
|---|---|---|---|---|
| 1 | 7.88 | 403.67 | 11.23 | 100.00 |
| 2 | 8.69 | 252.55 | 10.18 | 62.56 |
| 3 | 11.37 | 182.85 | 7.78 | 45.30 |

TABLE 2-continued

XRPD pattern analysis data for crystalline form B

| No. | 2-theta value (°) | Peak height (cts) | Interplanar spacing (Å) | Relative intensity (%) |
|---|---|---|---|---|
| 4 | 12.47 | 201.17 | 7.10 | 49.83 |
| 5 | 15.32 | 109.84 | 5.78 | 27.21 |
| 6 | 16.45 | 342.49 | 5.39 | 84.84 |
| 7 | 17.49 | 247.35 | 5.07 | 61.27 |
| 8 | 20.04 | 65.15 | 4.43 | 16.14 |
| 9 | 21.24 | 105.60 | 4.18 | 26.16 |
| 10 | 22.90 | 118.92 | 3.88 | 29.46 |
| 11 | 23.71 | 97.90 | 3.75 | 24.25 |
| 12 | 24.14 | 94.56 | 3.69 | 23.42 |
| 13 | 24.90 | 72.68 | 3.58 | 18.00 |

In some embodiments of the present disclosure, the crystalline form B described above has a differential scanning calorimetry curve with on-set points of endothermic peaks at 156.1±3° C. and 207.3±3° C. and an exothermic peak at 168.6±3° C.

In some embodiments of the present disclosure, the crystalline form B described above has a DSC pattern as shown in FIG. 5.

In some embodiments of the present disclosure, the crystalline form B described above has a thermogravimetric analysis curve with a weight loss of up to 9.8% at 115.0±3° C. and a further weigh loss of up to 1.84% at 170.0±3° C.

In some embodiments of the present disclosure, the crystalline form B described above has a TGA pattern as shown in FIG. 6.

The present disclosure further provides a crystalline form C of the compound 1 having diffraction peaks in an X-ray powder diffraction pattern at the following 2-theta values: 7.81±0.20°, 8.31±0.20° and 11.21±0.20°.

In some embodiments of the present disclosure, the crystalline form C of the compound 1 described above has diffraction peaks in an X-ray powder diffraction pattern at the following 2-theta values: 7.81±0.20°, 8.31±0.20°, 11.21±0.20°, 14.58±0.20°, 16.37±0.20°, 17.92±0.20°, 23.48±0.20° and 24.18±0.20°.

In some embodiments of the present disclosure, the crystalline form C of the compound 1 described above has an XRPD pattern as shown in FIG. 7.

In some embodiments of the present disclosure, the crystalline form C described above has XRPD pattern analysis data as shown in Table 3:

TABLE 3

XRPD pattern analysis data for crystalline form C

| No. | 2-theta value (°) | Peak height (cts) | Interplanar spacing (Å) | Relative intensity (%) |
|---|---|---|---|---|
| 1 | 7.81 | 237.55 | 11.31 | 20.90 |
| 2 | 8.31 | 1136.48 | 10.64 | 100.00 |
| 3 | 11.21 | 204.30 | 7.90 | 17.98 |
| 4 | 14.58 | 199.20 | 6.07 | 17.53 |
| 5 | 16.37 | 91.97 | 5.42 | 8.09 |
| 6 | 17.92 | 62.57 | 4.95 | 5.51 |
| 7 | 23.48 | 60.57 | 3.79 | 5.33 |
| 8 | 24.18 | 75.73 | 3.68 | 6.66 |

In some embodiments of the present disclosure, the crystalline form C described above has a differential scanning calorimetry curve with on-set points of endothermic peaks at 129.6±3° C. and 197.1±3° C. and an exothermic peak at 149.7±3° C.

In some embodiments of the present disclosure, the crystalline form C described above has a DSC pattern as shown in FIG. 8.

In some embodiments of the present disclosure, the crystalline form C described above has a thermogravimetric analysis curve with a weight loss of up to 13.05% at 170.0±3° C.

In some embodiments of the present disclosure, the crystalline form C described above has a TGA pattern as shown in FIG. 9.

The present disclosure further provides a crystalline form D of the compound 1 having diffraction peaks in an X-ray powder diffraction pattern at the following 2-theta values: 8.86±0.20°, 12.77±0.20° and 22.89±0.20°.

In some embodiments of the present disclosure, the crystalline form D of the compound 1 described above has diffraction peaks in an X-ray powder diffraction pattern at the following 2-theta values: 7.63±0.20°, 8.86±0.20°, 10.12±0.20°, 11.53±0.20°, 12.77±0.20°, 18.02±0.20° and 22.89±0.20°.

In some embodiments of the present disclosure, the crystalline form D of the compound 1 described above has an XRPD pattern as shown in FIG. 10.

In some embodiments of the present disclosure, the crystalline form D described above has XRPD pattern analysis data as shown in Table 4:

TABLE 4

XRPD pattern analysis data for crystalline form D

| No. | 2-theta value (°) | Peak height (cts) | Interplanar spacing (Å) | Relative intensity (%) |
|---|---|---|---|---|
| 1 | 7.63 | 68.37 | 11.58 | 5.42 |
| 2 | 8.86 | 1262.06 | 9.98 | 100.00 |
| 3 | 10.12 | 96.97 | 8.74 | 7.68 |
| 4 | 11.53 | 90.20 | 7.67 | 7.15 |
| 5 | 12.77 | 125.20 | 6.93 | 9.92 |
| 6 | 18.02 | 81.81 | 4.92 | 6.48 |
| 7 | 22.89 | 103.18 | 3.89 | 8.18 |

In some embodiments of the present disclosure, the crystalline form D described above has a differential scanning calorimetry curve with on-set points of endothermic peaks at 142.6±3° C. and 197.2±3° C. and an exothermic peak at 168.4±3° C.

In some embodiments of the present disclosure, the crystalline form D described above has a DSC pattern as shown in FIG. 11.

In some embodiments of the present disclosure, the crystalline form D described above has a thermogravimetric analysis curve with a weight loss of up to 3.00% at 115.0±3° C. and a further weigh loss of up to 4.14% at 170.0±3° C.

In some embodiments of the present disclosure, the crystalline form D described above has a TGA pattern as shown in FIG. 12.

The present disclosure further provides a crystalline form E of the compound 1 having diffraction peaks in an X-ray powder diffraction pattern at the following 2-theta values: 8.22±0.20°, 11.45±0.20° and 16.66±0.20°.

In some embodiments of the present disclosure, the crystalline form E of the compound 1 described above has diffraction peaks in an X-ray powder diffraction pattern at the following 2-theta values: 8.22±0.20°, 8.84±0.20°, 11.45±0.20°, 12.23±0.20°, 13.16±0.20°, 16.66±0.20°, 18.57±0.20° and 24.48±0.20°.

In some embodiments of the present disclosure, the crystalline form E of the compound 1 described above has an XRPD pattern as shown in FIG. 13.

In some embodiments of the present disclosure, the crystalline form E described above has XRPD pattern analysis data as shown in Table 5:

TABLE 5

XRPD pattern analysis data for crystalline form E

| No. | 2-theta value (°) | Peak height (cts) | Interplanar spacing (Å) | Relative intensity (%) |
|---|---|---|---|---|
| 1 | 8.22 | 131.05 | 10.75 | 84.73 |
| 2 | 8.84 | 128.73 | 10.00 | 83.22 |
| 3 | 11.45 | 154.68 | 7.73 | 100.00 |
| 4 | 12.23 | 82.07 | 7.24 | 53.06 |
| 5 | 13.16 | 52.37 | 6.73 | 33.86 |
| 6 | 16.66 | 134.61 | 5.32 | 87.03 |
| 7 | 18.57 | 67.74 | 4.78 | 43.80 |
| 8 | 24.48 | 46.61 | 3.64 | 30.13 |

In some embodiments of the present disclosure, the crystalline form E described above has a differential scanning calorimetry curve with on-set points of endothermic peaks at 161.1±3° C. and 209.3±3° C. and an exothermic peak at 168.9±3° C.

In some embodiments of the present disclosure, the crystalline form E described above has a DSC pattern as shown in FIG. 14.

In some embodiments of the present disclosure, the crystalline form E described above has a thermogravimetric analysis curve with a weight loss of up to 8.91% at 115.0±3° C. and a further weigh loss of up to 1.41% at 170.0±3° C.

In some embodiments of the present disclosure, the crystalline form E described above has a TGA pattern as shown in FIG. 15.

The present disclosure further provides a crystalline form F of the compound 1 having diffraction peaks in an X-ray powder diffraction pattern at the following 2-theta values: 12.20±0.20°, 16.21±0.20° and 17.24±0.20°.

The present disclosure further provides a crystalline form F of the compound 1 having diffraction peaks in an X-ray powder diffraction pattern at the following 2-theta values: 16.21±0.20°, 16.70±0.20° and 17.24±0.20°.

In some embodiments of the present disclosure, the crystalline form F of the compound 1 described above has diffraction peaks in an X-ray powder diffraction pattern at the following 2-theta values: 7.62±0.20°, 11.11±0.20°, 12.20±0.20°, 15.07±0.20°, 16.21±0.20°, 16.70±0.20°, 17.24±0.20° and 19.81±0.20°.

In some embodiments of the present disclosure, the crystalline form F of the compound 1 described above has diffraction peaks in an X-ray powder diffraction pattern at the following 2-theta values: 7.62°, 8.44°, 9.61°, 11.11°, 12.20°, 12.76°, 14.82°, 15.07°, 16.21°, 16.70°, 17.24°, 18.32°, 19.81°, 20.99°, 21.69°, 22.69°, 23.51°, 23.89°, 24.34°, 24.69°, 25.32°, 25.99°, 27.06°, 27.54°, 28.65°, 30.57°, 33.43° and 34.16°.

In some embodiments of the present disclosure, the crystalline form F of the compound 1 described above has an XRPD pattern as shown in FIG. 16.

In some embodiments of the present disclosure, the crystalline form F described above has XRPD pattern analysis data as shown in Table 6:

TABLE 6

XRPD pattern analysis data for crystalline form F

| No. | 2-theta value (°) | Peak height (cts) | Interplanar spacing (Å) | Relative intensity (%) |
|---|---|---|---|---|
| 1 | 7.62 | 400.68 | 11.60 | 30.73 |
| 2 | 8.44 | 469.65 | 10.48 | 36.02 |
| 3 | 9.61 | 95.82 | 9.21 | 7.35 |
| 4 | 11.11 | 723.15 | 7.97 | 55.46 |
| 5 | 12.20 | 608.87 | 7.26 | 46.70 |
| 6 | 12.76 | 213.41 | 6.94 | 16.37 |
| 7 | 14.82 | 355.71 | 5.98 | 27.28 |
| 8 | 15.07 | 509.45 | 5.88 | 39.07 |
| 9 | 16.21 | 1303.89 | 5.47 | 100.00 |
| 10 | 16.70 | 828.97 | 5.31 | 63.58 |
| 11 | 17.24 | 979.25 | 5.14 | 75.10 |
| 12 | 18.32 | 487.12 | 4.84 | 37.36 |
| 13 | 19.81 | 508.79 | 4.48 | 39.02 |
| 14 | 20.99 | 497.53 | 4.23 | 38.16 |
| 15 | 21.69 | 306.44 | 4.10 | 23.50 |
| 16 | 22.69 | 484.18 | 3.92 | 37.13 |
| 17 | 23.51 | 383.14 | 3.78 | 29.38 |
| 18 | 23.89 | 400.62 | 3.72 | 30.73 |
| 19 | 24.34 | 457.48 | 3.66 | 35.09 |
| 20 | 24.69 | 317.92 | 3.61 | 24.38 |
| 21 | 25.32 | 246.49 | 3.52 | 18.90 |
| 22 | 25.99 | 87.34 | 3.43 | 6.70 |
| 23 | 27.06 | 229.88 | 3.30 | 17.63 |
| 24 | 27.54 | 111.35 | 3.24 | 8.54 |
| 25 | 28.65 | 86.08 | 3.12 | 6.60 |
| 26 | 30.57 | 37.73 | 2.92 | 2.89 |
| 27 | 33.43 | 54.15 | 2.68 | 4.15 |
| 28 | 34.16 | 41.91 | 2.63 | 3.21 |

In some embodiments of the present disclosure, the crystalline form F described above has a differential scanning calorimetry curve with on-set points of endothermic peaks at 158.9±3° C. and 209.0±3° C. and an exothermic peak at 169.2±3° C.

In some embodiments of the present disclosure, the crystalline form F described above has a DSC pattern as shown in FIG. 17.

In some embodiments of the present disclosure, the crystalline form F described above has a thermogravimetric analysis curve with a weight loss of 4.61% at 115.0±3° C. and a further weigh loss of 1.26% at 170.0±3° C.

In some embodiments of the present disclosure, the crystalline form F described above has a TGA pattern as shown in FIG. 18.

The present disclosure further provides a crystalline form G of the compound 1 having diffraction peaks in an X-ray powder diffraction pattern at the following 2-theta values: 14.75±0.20°, 16.64±0.20° and 18.94±0.20°.

In some embodiments of the present disclosure, the crystalline form G of the compound 1 described above has diffraction peaks in an X-ray powder diffraction pattern at the following 2-theta values: 3.74±0.20°, 8.56±0.20°, 14.75±0.20°, 16.64±0.20°, 17.10±0.20°, 18.94±0.20°, 20.10±0.20° and 20.98±0.20°.

In some embodiments of the present disclosure, the crystalline form G of the compound 1 described above has diffraction peaks in an X-ray powder diffraction pattern at the following 2-theta values: 3.74°, 8.56°, 11.08°, 13.06°, 13.47°, 14.75°, 15.13°, 15.87°, 16.64°, 17.10°, 17.39°, 18.45°, 18.94°, 19.61°, 20.10°, 20.98°, 22.41°, 22.93°, 23.49°, 24.27°, 25.63°, 28.22°, 29.66°, 32.10° and 34.43°. In some embodiments of the present disclosure, the crystalline form G of the compound 1 described above has an XRPD pattern as shown in FIG. 19.

In some embodiments of the present disclosure, the crystalline form G described above has XRPD pattern analysis data as shown in Table 7:

TABLE 7

XRPD pattern analysis data for crystalline form G

| No. | 2-theta value (°) | Peak height (cts) | Interplanar spacing (Å) | Relative intensity (%) |
|---|---|---|---|---|
| 1 | 3.74 | 430.37 | 23.61 | 61.17 |
| 2 | 8.56 | 419.38 | 10.32 | 59.61 |
| 3 | 11.08 | 168.77 | 7.99 | 23.99 |
| 4 | 13.06 | 199.44 | 6.78 | 28.35 |
| 5 | 13.47 | 95.89 | 6.57 | 13.63 |
| 6 | 14.75 | 649.24 | 6.01 | 92.28 |
| 7 | 15.13 | 369.75 | 5.86 | 52.55 |
| 8 | 15.87 | 149.63 | 5.58 | 21.27 |
| 9 | 16.64 | 607.61 | 5.33 | 86.36 |
| 10 | 17.10 | 261.97 | 5.19 | 37.23 |
| 11 | 17.39 | 212.14 | 5.10 | 30.15 |
| 12 | 18.45 | 178.62 | 4.81 | 25.39 |
| 13 | 18.94 | 703.59 | 4.68 | 100.00 |
| 14 | 19.61 | 216.41 | 4.53 | 30.76 |
| 15 | 20.10 | 325.47 | 4.42 | 46.26 |
| 16 | 20.98 | 546.70 | 4.23 | 77.70 |
| 17 | 22.41 | 226.66 | 3.97 | 32.21 |
| 18 | 22.93 | 37.51 | 3.88 | 5.33 |
| 19 | 23.49 | 266.03 | 3.79 | 37.81 |
| 20 | 24.27 | 60.63 | 3.67 | 8.62 |
| 21 | 25.63 | 251.40 | 3.48 | 35.73 |
| 22 | 28.22 | 82.00 | 3.16 | 11.65 |
| 23 | 29.66 | 132.30 | 3.01 | 18.80 |
| 24 | 32.10 | 36.74 | 2.79 | 5.22 |
| 25 | 34.43 | 84.64 | 2.60 | 12.03 |

In some embodiments of the present disclosure, the crystalline form G described above has a differential scanning calorimetry curve with on-set points of endothermic peaks at 92.3±3° C. and 217.6±3° C.

In some embodiments of the present disclosure, the crystalline form G described above has a DSC pattern as shown in FIG. 20.

In some embodiments of the present disclosure, the crystalline form G described above has a thermogravimetric analysis curve with a weight loss of 3.32% at 170.0±3° C.

In some embodiments of the present disclosure, the crystalline form G described above has a TGA pattern as shown in FIG. 21.

The present disclosure further provides a compound 2.

Compound 1•*y* $H_3PO_4$ 2 wherein y is 0.9-1.1, preferably 0.91, 1 or 1.1.

The present disclosure further provides a crystalline form H of the compound 2 having diffraction peaks in an X-ray powder diffraction pattern at the following 2-theta values: 17.11±0.20°, 18.69±0.20° and 20.74±0.20°.

In some embodiments of the present disclosure, the crystalline form H of the compound 2 described above has diffraction peaks in an X-ray powder diffraction pattern at the following 2-theta values: 11.33±0.20°, 12.46±0.20°, 14.04±0.20°, 14.99±0.20°, 17.11±0.20°, 18.69±0.20°, 20.74±0.20° and 22.75±0.20°.

In some embodiments of the present disclosure, the crystalline form H of the compound 2 described above has an XRPD pattern as shown in FIG. 22.

In some embodiments of the present disclosure, the crystalline form H described above has XRPD pattern analysis data as shown in Table 8:

TABLE 8

XRPD pattern analysis data for crystalline form H

| No. | 2-theta value (°) | Peak height (cts) | Interplanar spacing (Å) | Relative intensity (%) |
|---|---|---|---|---|
| 1 | 11.33 | 73.56 | 7.81 | 22.51 |
| 2 | 12.46 | 77.66 | 7.11 | 23.77 |
| 3 | 14.04 | 114.18 | 6.31 | 34.94 |
| 4 | 14.99 | 69.75 | 5.91 | 21.34 |
| 5 | 17.11 | 326.78 | 5.18 | 100.00 |
| 6 | 18.69 | 153.89 | 4.75 | 47.09 |
| 7 | 20.74 | 221.53 | 4.28 | 67.79 |
| 8 | 22.75 | 100.09 | 3.91 | 30.63 |

In some embodiments of the present disclosure, the crystalline form H described above has a differential scanning calorimetry curve with on-set points of endothermic peaks at 77.7±3, 147.7±3° C. and 158.4±3° C.

In some embodiments of the present disclosure, the crystalline form H described above has a DSC pattern as shown in FIG. 23.

In some embodiments of the present disclosure, the crystalline form H described above has a thermogravimetric analysis curve with a weight loss of 2.09% at 75.0±3° C. and a further weigh loss of 9.01% at 175.0±3° C.

In some embodiments of the present disclosure, the crystalline form H described above has a TGA pattern as shown in FIG. 24.

The present disclosure further provides a compound 3.

Compound 1•*m* 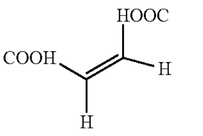 3 wherein m is 0.98-1.0, preferably 0.98 or 1.0.

The present disclosure further provides a crystalline form J of the compound 3 having diffraction peaks in an X-ray powder diffraction pattern at the following 2-theta values: 7.19±0.20°, 11.64±0.20° and 12.87±0.20°.

In some embodiments of the present disclosure, the crystalline form J of the compound 3 described above has diffraction peaks in an X-ray powder diffraction pattern at the following 2-theta values: 7.19±0.20°, 8.34±0.20°, 9.69±0.20°, 11.64±0.20°, 12.87±0.20°, 14.97±0.20°, 18.42±0.20° and 21.08±0.20°.

In some embodiments of the present disclosure, the crystalline form J of the compound 3 described above has diffraction peaks in an X-ray powder diffraction pattern at the following 2-theta values: 7.19°, 8.34°, 9.69°, 11.64°, 12.87°, 13.53°, 13.85°, 14.97°, 15.49°, 15.91°, 16.25°, 16.75°, 17.51°, 18.02°, 18.42°, 18.57°, 19.40°, 19.82°, 20.60°, 21.08°, 22.32°, 22.75°, 24.63°, 25.00°, 26.49°, 27.18°, 27.86°, 32.61° and 33.97°.

In some embodiments of the present disclosure, the crystalline form J of the compound 3 described above has an XRPD pattern as shown in FIG. 25.

In some embodiments of the present disclosure, the crystalline form J described above has XRPD pattern analysis data as shown in Table 9:

TABLE 9

XRPD pattern analysis data for crystalline form J

| No. | 2-theta value (°) | Peak height (cts) | Interplanar spacing (Å) | Relative intensity (%) |
|---|---|---|---|---|
| 1 | 7.19 | 428.20 | 12.29 | 37.84 |
| 2 | 8.34 | 247.23 | 10.60 | 21.85 |
| 3 | 9.69 | 394.96 | 9.13 | 34.90 |
| 4 | 11.64 | 617.56 | 7.60 | 54.57 |
| 5 | 12.87 | 1131.75 | 6.88 | 100.00 |
| 6 | 13.53 | 279.03 | 6.55 | 24.65 |
| 7 | 13.85 | 178.22 | 6.39 | 15.75 |
| 8 | 14.97 | 385.40 | 5.92 | 34.05 |
| 9 | 15.49 | 111.13 | 5.72 | 9.82 |
| 10 | 15.91 | 256.12 | 5.57 | 22.63 |
| 11 | 16.25 | 312.72 | 5.46 | 27.63 |
| 12 | 16.75 | 103.72 | 5.29 | 9.16 |
| 13 | 17.51 | 200.32 | 5.07 | 17.70 |
| 14 | 18.02 | 234.52 | 4.92 | 20.72 |
| 15 | 18.42 | 449.91 | 4.82 | 39.75 |
| 16 | 18.57 | 357.60 | 4.78 | 31.60 |
| 17 | 19.40 | 112.64 | 4.58 | 9.95 |
| 18 | 19.82 | 114.88 | 4.48 | 10.15 |
| 19 | 20.60 | 184.76 | 4.31 | 16.33 |
| 20 | 21.08 | 360.61 | 4.21 | 31.86 |
| 21 | 22.32 | 173.47 | 3.98 | 15.33 |
| 22 | 22.75 | 123.40 | 3.91 | 10.90 |
| 23 | 24.63 | 252.31 | 3.61 | 22.29 |
| 24 | 25.00 | 242.41 | 3.56 | 21.42 |
| 25 | 26.49 | 168.59 | 3.36 | 14.90 |
| 26 | 27.18 | 140.28 | 3.28 | 12.39 |
| 27 | 27.86 | 72.41 | 3.20 | 6.40 |
| 28 | 32.61 | 38.54 | 2.75 | 3.41 |
| 29 | 33.97 | 77.35 | 2.64 | 6.83 |

In some embodiments of the present disclosure, the crystalline form J described above has a differential scanning calorimetry curve with on-set points of endothermic peaks at 151.1±3° C. and 169.6±3° C.

In some embodiments of the present disclosure, the crystalline form J described above has a DSC pattern as shown in FIG. 26.

In some embodiments of the present disclosure, the crystalline form J described above has a thermogravimetric analysis curve with a weight loss of 3.00% at 130.0±3° C.

In some embodiments of the present disclosure, the crystalline form J described above has a TGA pattern as shown in FIG. 27.

The present disclosure further provides a compound 4.

Compound 1•*n* 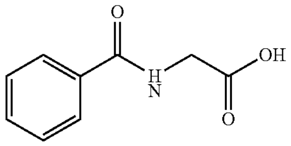 4 wherein n is 0.95-1.0, preferably 0.95 or 1.0.

The present disclosure further provides a crystalline form K of the compound 4 having diffraction peaks in an X-ray powder diffraction pattern at the following 2-theta values: 5.67±0.20°, 11.34±0.20° and 19.14±0.20°.

In some embodiments of the present disclosure, the crystalline form K of the compound 4 described above has diffraction peaks in an X-ray powder diffraction pattern at the following 2-theta values: 5.67±0.20°, 11.34±0.20°, 13.07±0.20°, 14.07±0.20°, 19.14±0.20°, 20.35±0.20°, 21.95±0.20° and 23.55±0.20°.

In some embodiments of the present disclosure, the crystalline form K of the compound 4 described above has diffraction peaks in an X-ray powder diffraction pattern at the following 2-theta values: 5.67°, 10.20°, 11.34°, 13.07°, 14.07°, 14.49°, 17.08°, 18.11°, 19.14°, 20.35°, 21.95°, 23.55°, 25.00°, 26.56° and 28.08°.

In some embodiments of the present disclosure, the crystalline form K of the compound 4 described above has an XRPD pattern as shown in FIG. 28.

In some embodiments of the present disclosure, the crystalline form K described above has XRPD pattern analysis data as shown in Table 10:

TABLE 10

XRPD pattern analysis data for crystalline form K

| No. | 2-theta value (°) | Peak height (cts) | Interplanar spacing (Å) | Relative intensity (%) |
|---|---|---|---|---|
| 1 | 5.67 | 668.47 | 15.59 | 100.00 |
| 2 | 10.20 | 123.82 | 8.67 | 18.52 |
| 3 | 11.34 | 476.51 | 7.80 | 71.28 |
| 4 | 13.07 | 199.54 | 6.78 | 29.85 |
| 5 | 14.07 | 152.20 | 6.29 | 22.77 |
| 6 | 14.49 | 72.20 | 6.11 | 10.80 |
| 7 | 17.08 | 135.50 | 5.19 | 20.27 |
| 8 | 18.11 | 229.38 | 4.90 | 34.31 |
| 9 | 19.14 | 405.41 | 4.64 | 60.65 |
| 10 | 20.35 | 252.68 | 4.36 | 37.80 |
| 11 | 21.95 | 394.94 | 4.05 | 59.08 |
| 12 | 23.55 | 192.94 | 3.78 | 28.86 |
| 13 | 25.00 | 70.65 | 3.56 | 10.57 |
| 14 | 26.56 | 77.43 | 3.36 | 11.58 |
| 15 | 28.08 | 140.86 | 3.18 | 21.07 |

In some embodiments of the present disclosure, the crystalline form K described above has a differential scanning calorimetry curve with on-set points of endothermic peaks at 114.6±3° C. and 158.4±3° C.

In some embodiments of the present disclosure, the crystalline form K described above has a DSC pattern as shown in FIG. 29.

In some embodiments of the present disclosure, the crystalline form K described above has a thermogravimetric analysis curve with a weight loss of 4.76% at 150.0±3° C.

In some embodiments of the present disclosure, the crystalline form K described above has a TGA pattern as shown in FIG. 30.

The present disclosure also provides a method for preparing the crystalline form A comprising adding the compound 1 into methanol, ethanol, water or a mixed solvent of an alcohol and water, and recrystallizing or slurrying to give the crystalline form A.

In some embodiments of the present disclosure, the alcohol solvent described above is selected from methanol.

In some embodiments of the present disclosure, in the mixed solvent of the alcohol solvent and water described above, the volume ratio of the alcohol solvent to water is selected from 1:(0-1.5). The present disclosure also provides use of the crystalline forms described above in preparing a medicament for treating CXCR2 related diseases.

TECHNICAL EFFECTS

The crystalline form A of the compound 1 disclosed herein has good stability and desirable druggability. It has significant inhibitory effect on CXCR2 receptor. In a rat COPD (chronic obstructive pulmonary disease) model constructed by retrolingual instillation of porcine pancreatic elastase (PPE), the crystalline form A of the compound 1 can significantly reduce the number of neutrophils and significantly improve the pulmonary function.

Definitions and Description

Unless otherwise stated, the following terms and phrases used herein are intended to have the following meanings. A particular phrase or term, unless otherwise specifically defined, should not be considered as uncertain or unclear, but construed according to its common meaning. When referring to a trade name, it is intended to refer to its corresponding commercial product or its active ingredient.

The intermediate compounds disclosed herein can be prepared by a variety of synthetic methods well known to those skilled in the art, including the specific embodiments listed below, embodiments formed by combinations thereof with other chemical synthetic methods, and equivalent substitutions thereof known to those skilled in the art. Preferred embodiments include, but are not limited to, the examples disclosed herein.

The chemical reactions of the specific embodiments disclosed herein are carried out in a suitable solvent that must be suitable for the chemical changes in the present disclosure and the reagents and materials required. In order to obtain the compounds disclosed herein, it is sometimes necessary for those skilled in the art to modify or select a synthesis procedure or a reaction scheme based on the existing embodiments.

The present disclosure is described in detail below by way of examples, which are not intended to limit the present disclosure in any way.

All solvents used in the present disclosure are commercially available and can be used without further purification.

The solvents used in the present disclosure are all commercial available. The following abbreviations are used herein: DMSO for dimethyl sulfoxide; PEG400 for polyethylene glycol 400; HP-β-CD for hydroxypropyl-β-cyclodextrin; PPE for porcine pancreatic elastase.

X-RAY POWDER DIFFRACTION (XRPD) METHODOLOGY OF THE PRESENT DISCLOSURE

Figure 1:
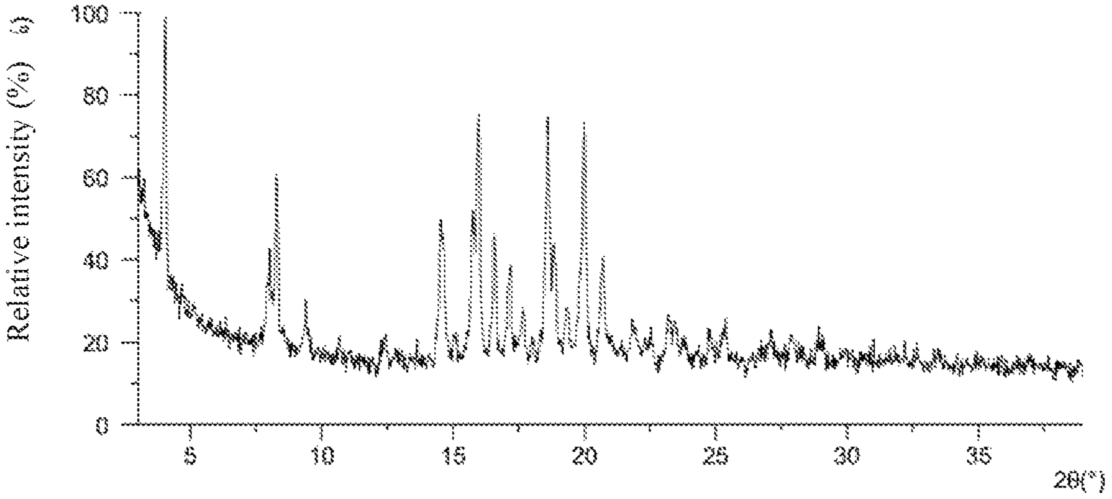
FIG. 1 is an XRPD pattern using Cu-Kα radiation of the crystalline form A of the compound 1.
Figure 2:
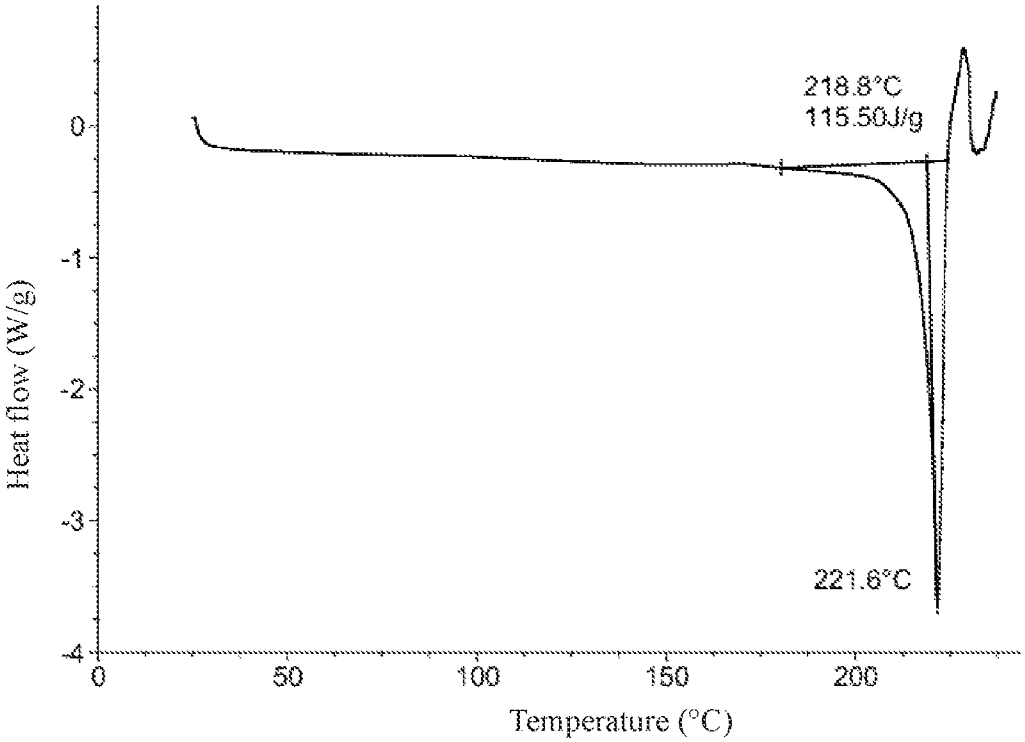
FIG. 2 is a DSC pattern of the crystalline form A of the compound 1.
Figure 3:
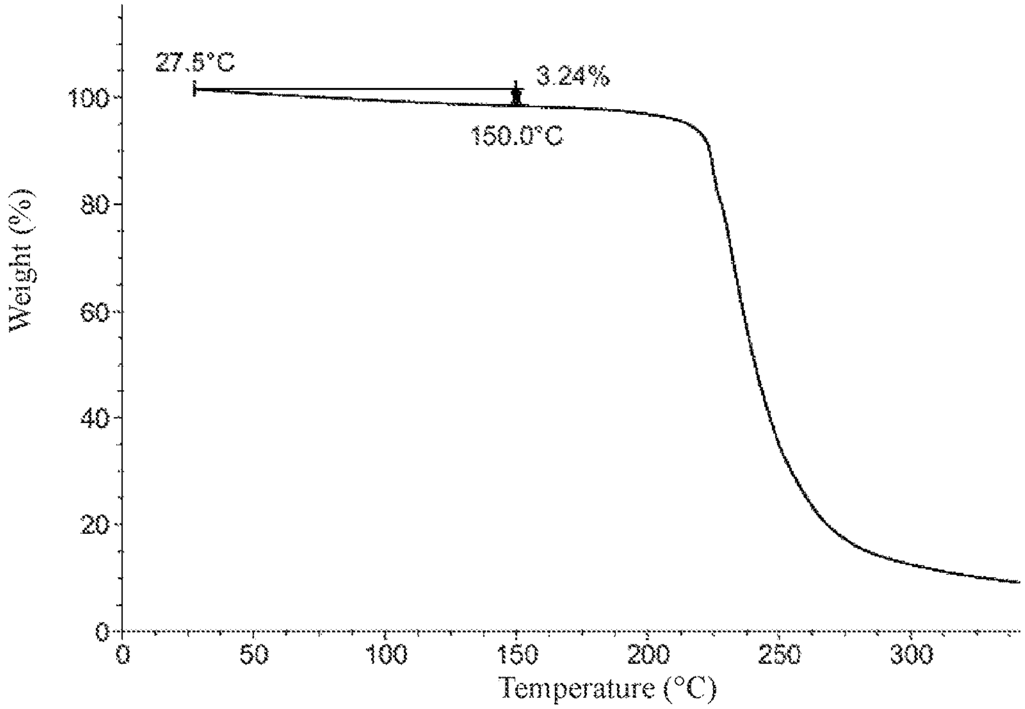
FIG. 3 is a TGA pattern of the crystalline form A of the compound 1.
Figure 4:
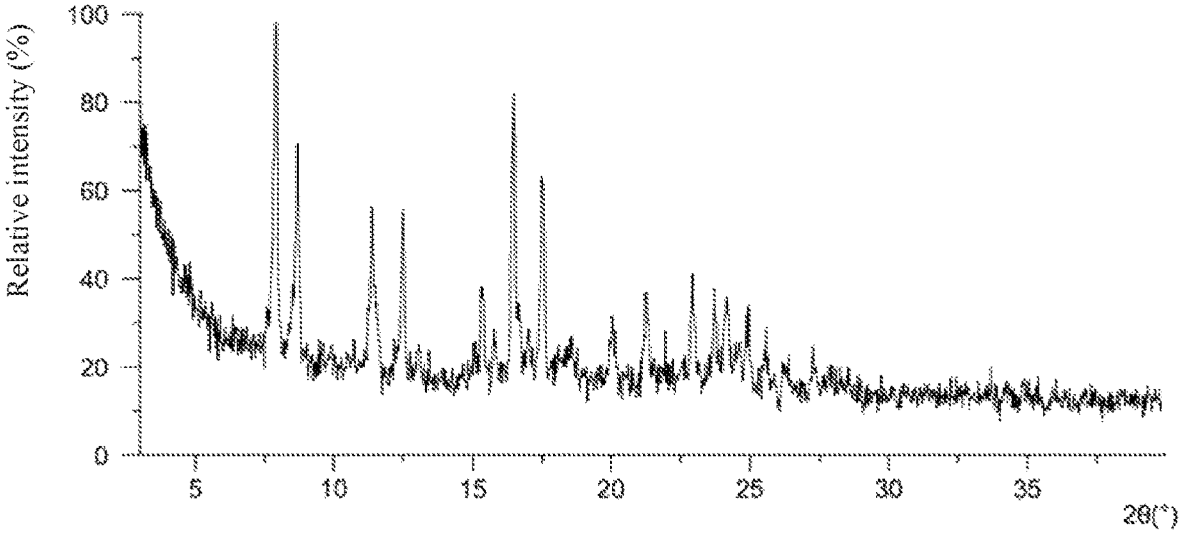
FIG. 4 is an XRPD pattern using Cu-Kα radiation of the crystalline form B of the compound 1.
Figure 5:
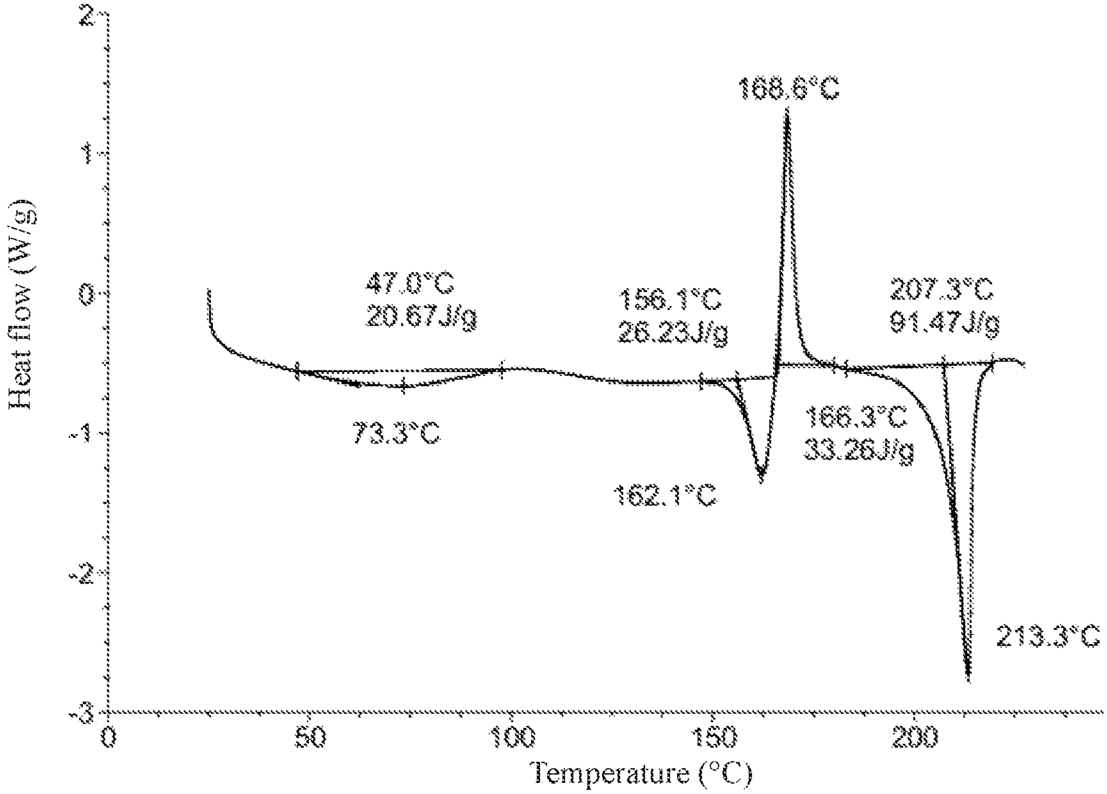
FIG. 5 is a DSC pattern of the crystalline form B of the compound 1.
Figure 6:
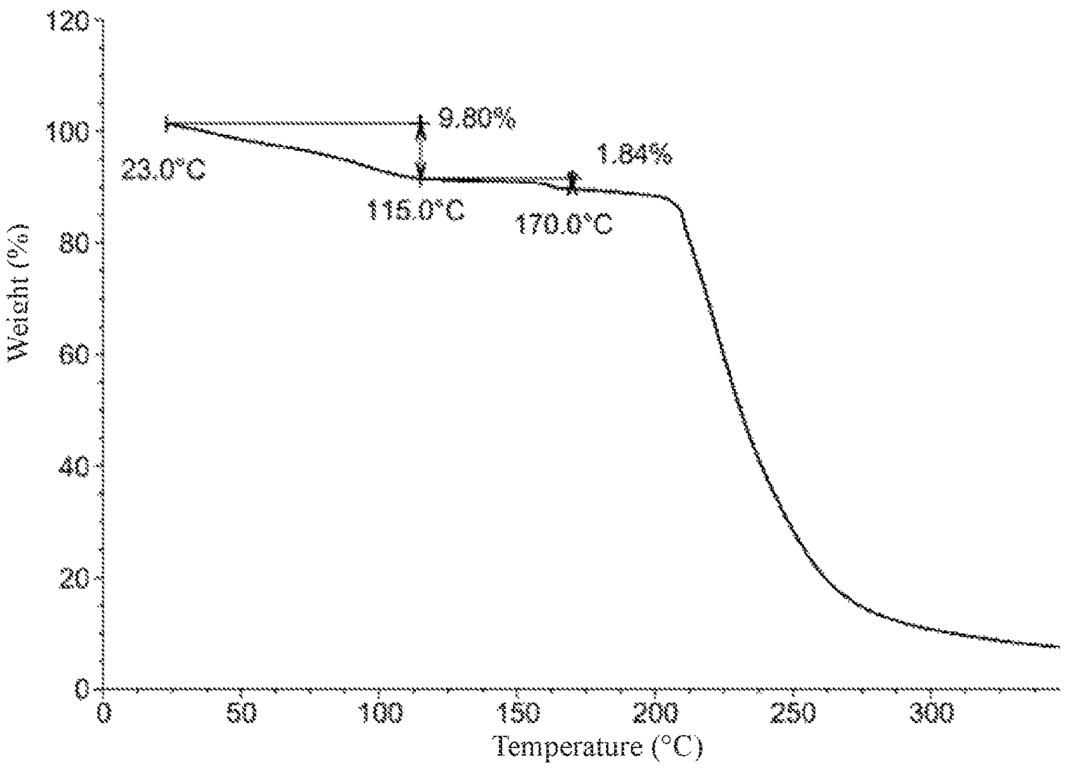
FIG. 6 is a TGA pattern of the crystalline form B of the compound 1.
Figure 7:
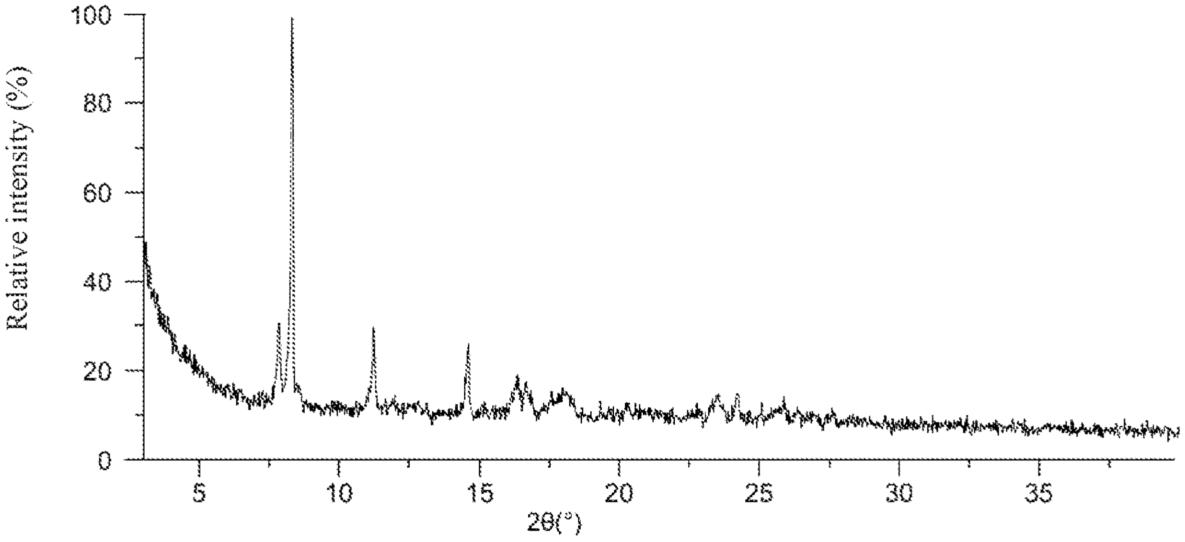
FIG. 7 is an XRPD pattern using Cu-Kα radiation of the crystalline form C of the compound 1.
Figure 8:
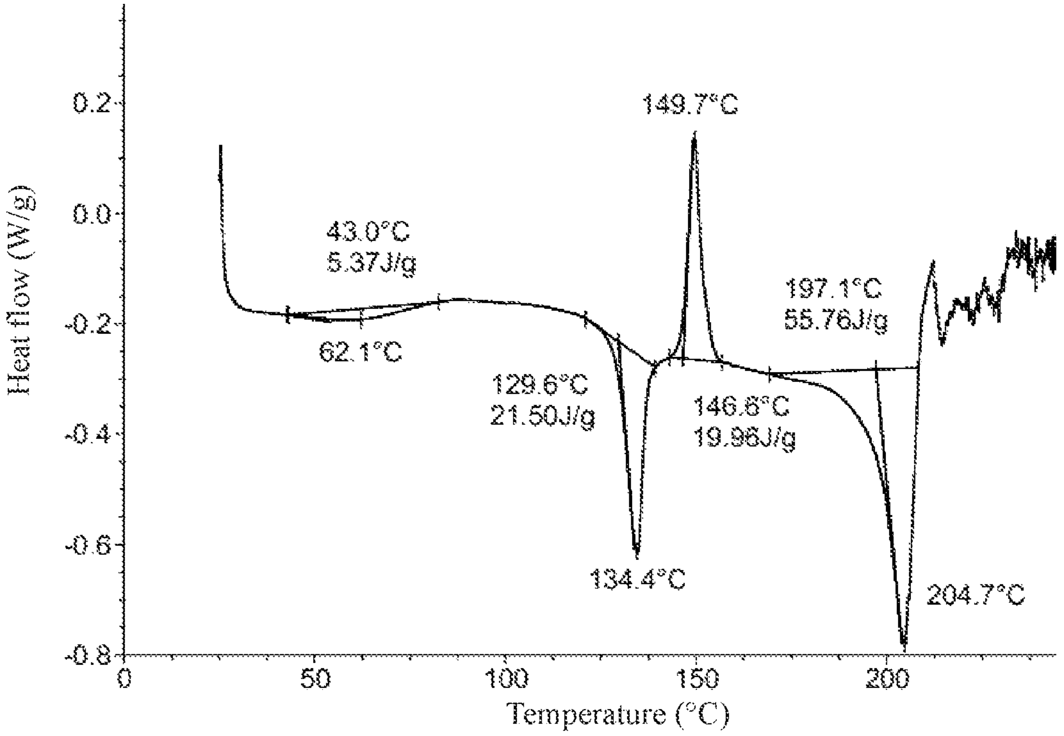
FIG. 8 is a DSC pattern of the crystalline form C of the compound 1.
Figure 9:
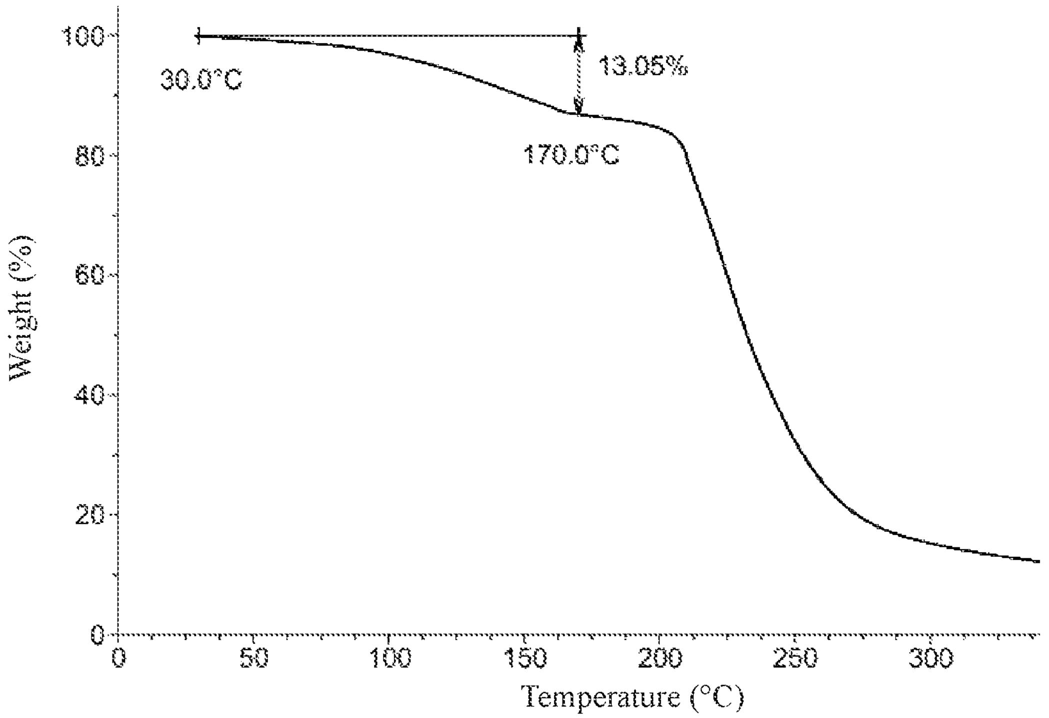
FIG. 9 is a TGA pattern of the crystalline form C of the compound 1.
Figure 10:
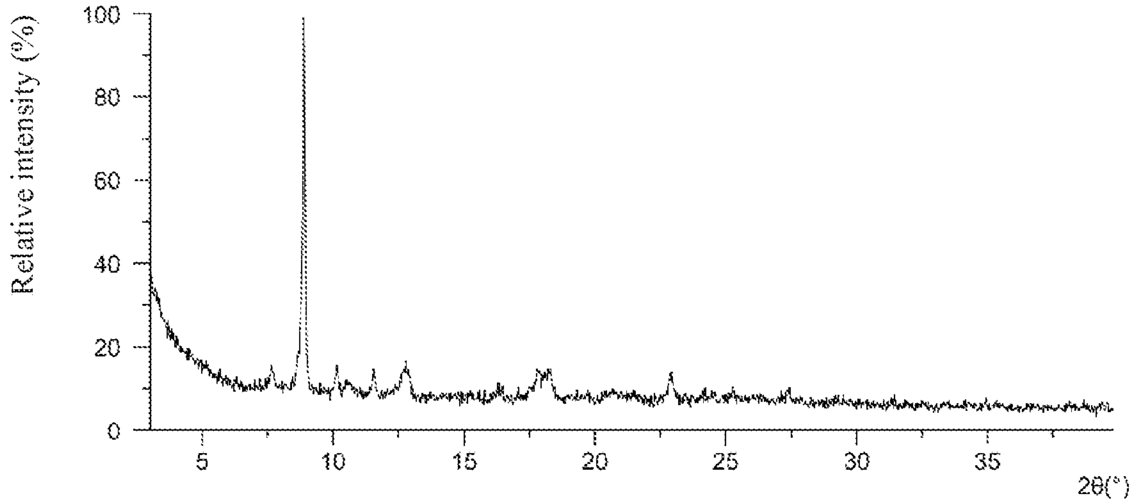
FIG. 10 is an XRPD pattern using Cu-Kα radiation of the crystalline form D of the compound 1.
Figure 11:
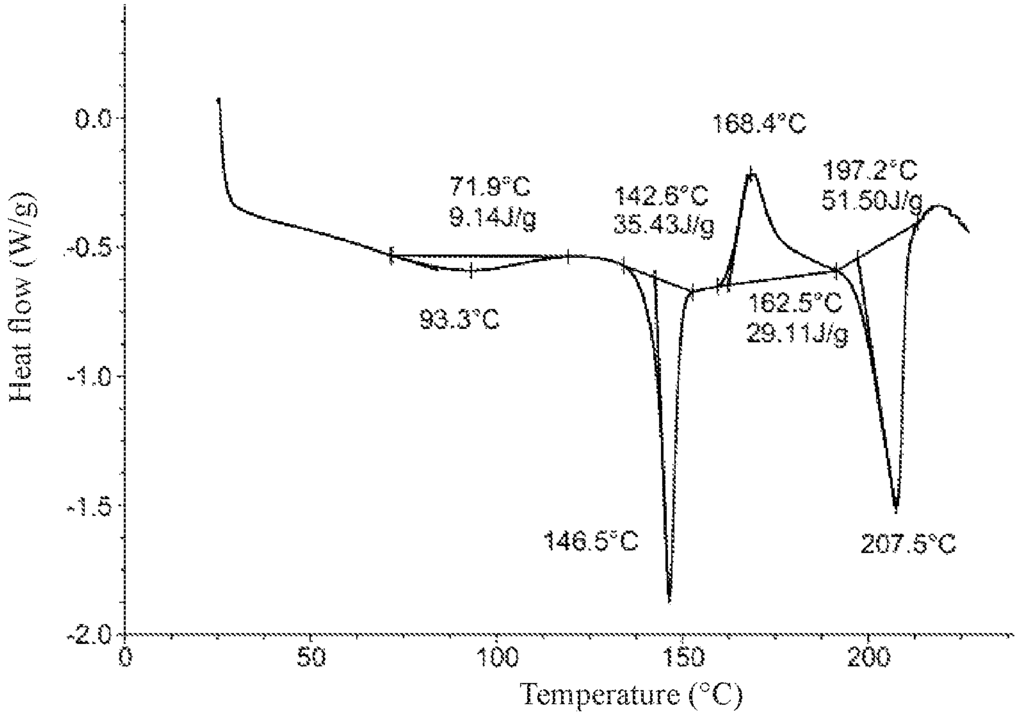
FIG. 11 is a DSC pattern of the crystalline form D of the compound 1.
Figure 12:
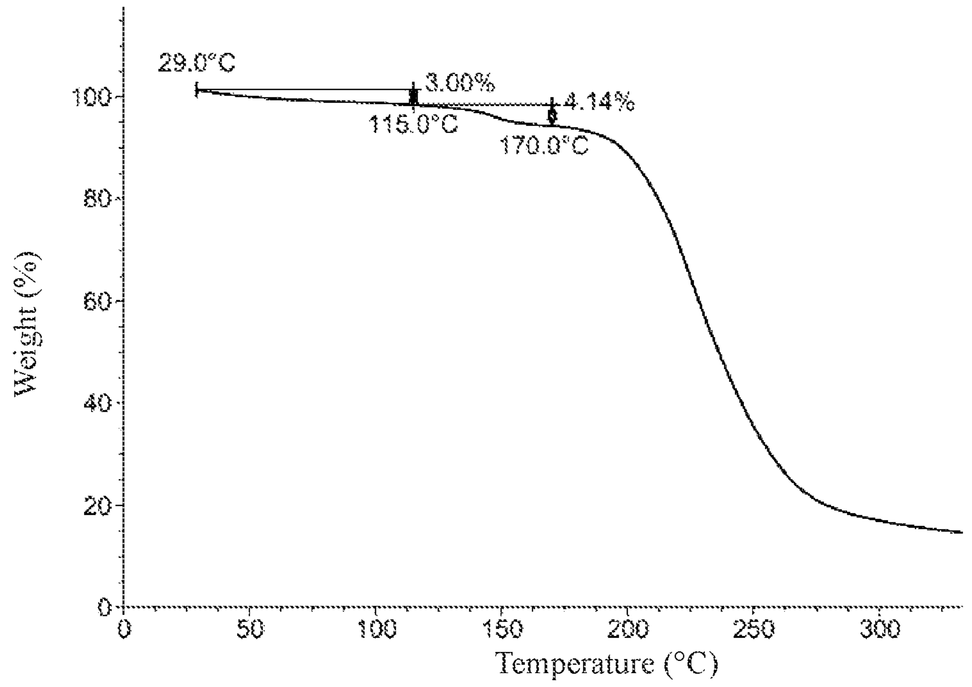
FIG. 12 is a TGA pattern of the crystalline form D of the compound 1.
Figure 13:
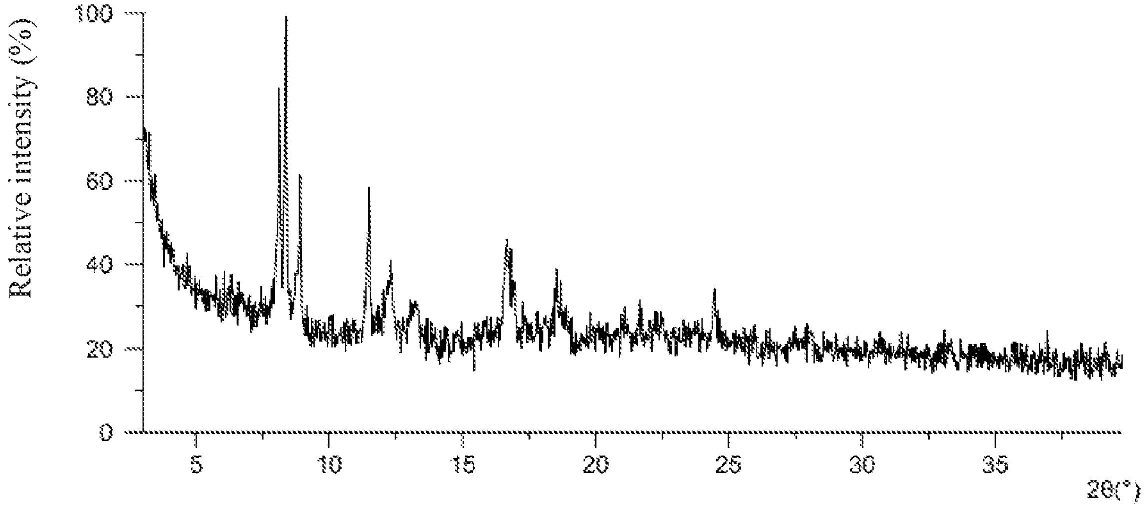
FIG. 13 is an XRPD pattern using Cu-Kα radiation of the crystalline form E of the compound 1.
Figure 14:
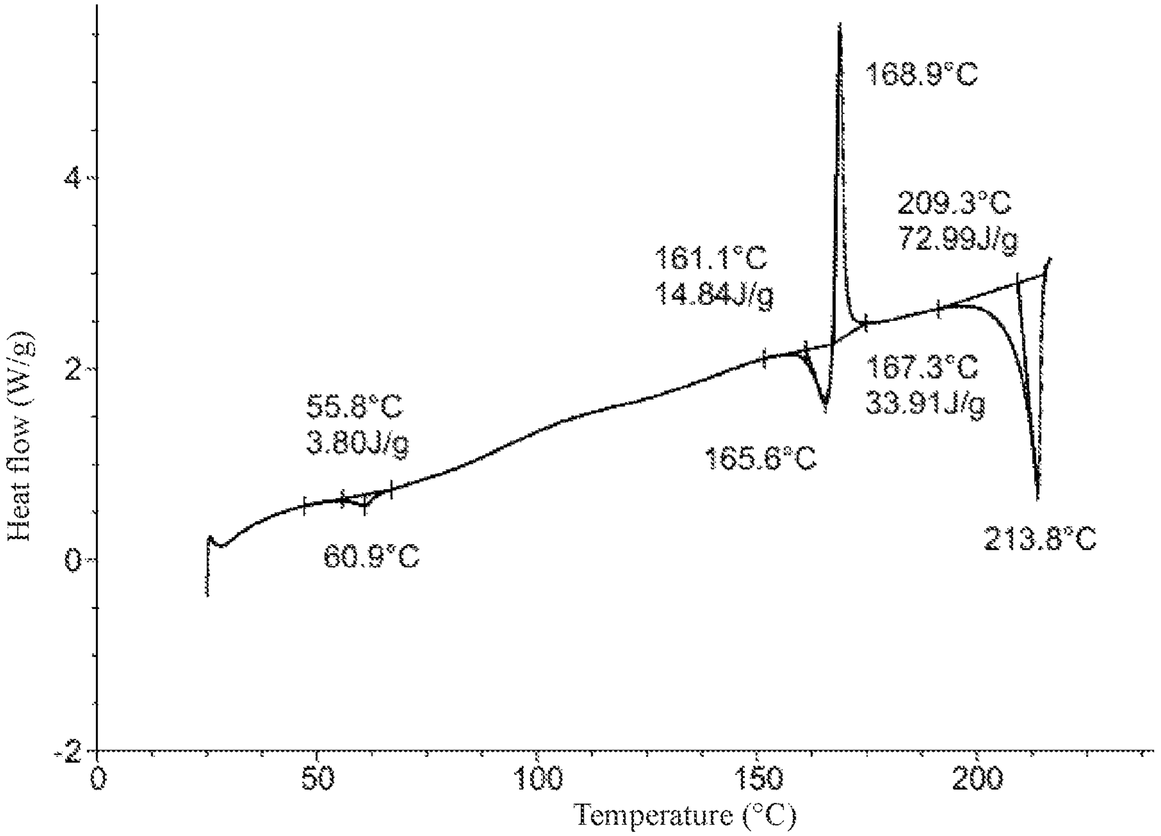
FIG. 14 is a DSC pattern of the crystalline form E of the compound 1.
Figure 15:
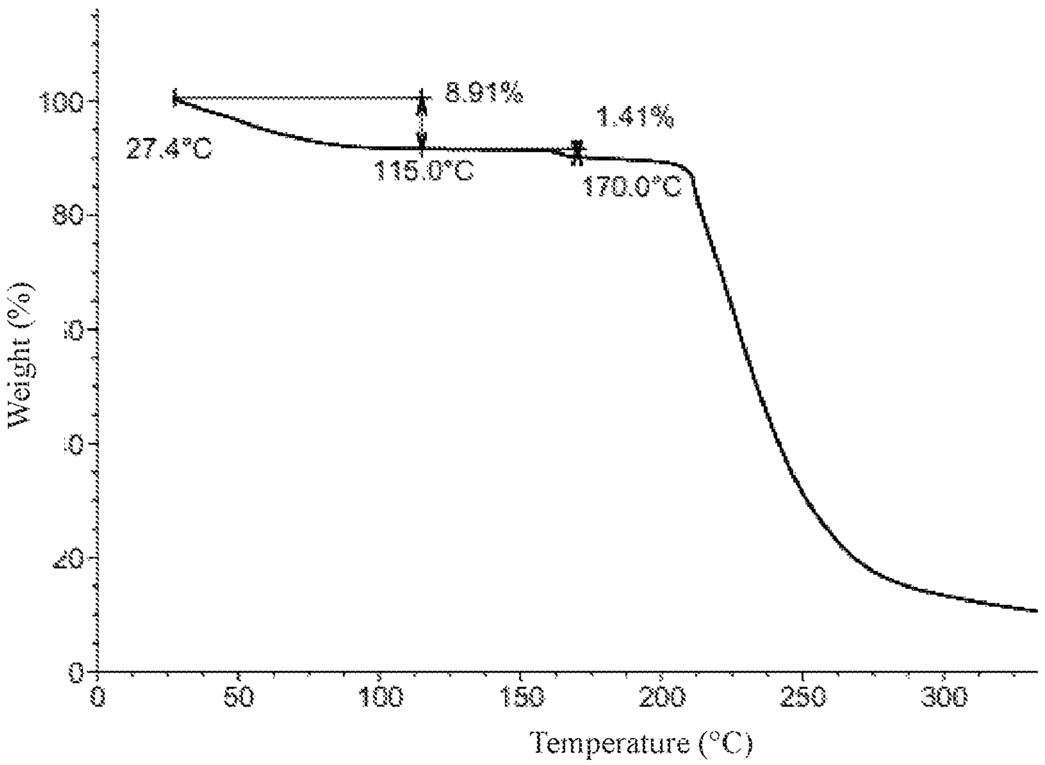
FIG. 15 is a TGA pattern of the crystalline form E of the compound 1.
Figure 16:
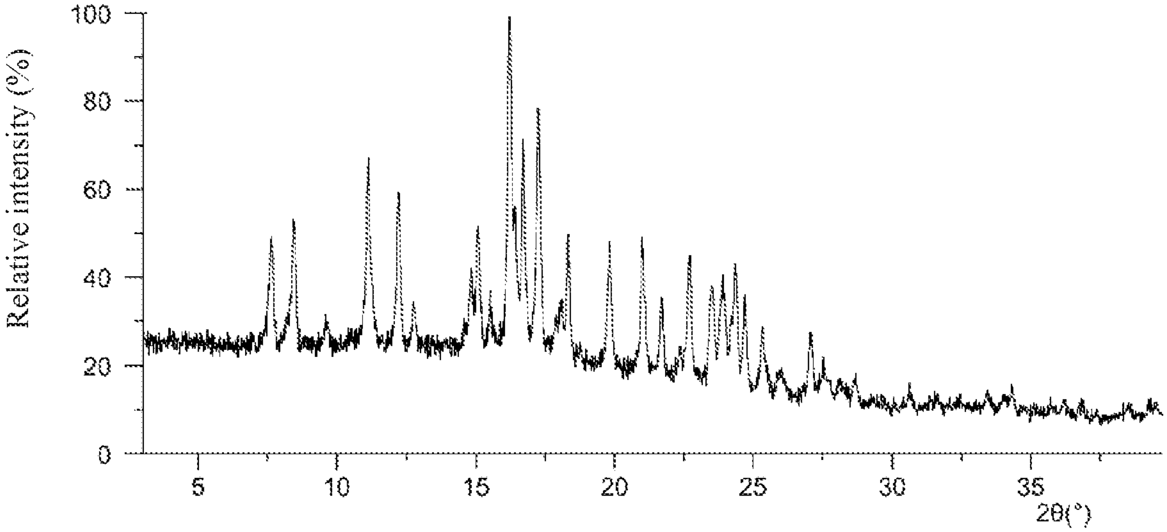
FIG. 16 is an XRPD pattern using Cu-Kα radiation of the crystalline form F of the compound 1.
Figure 17:
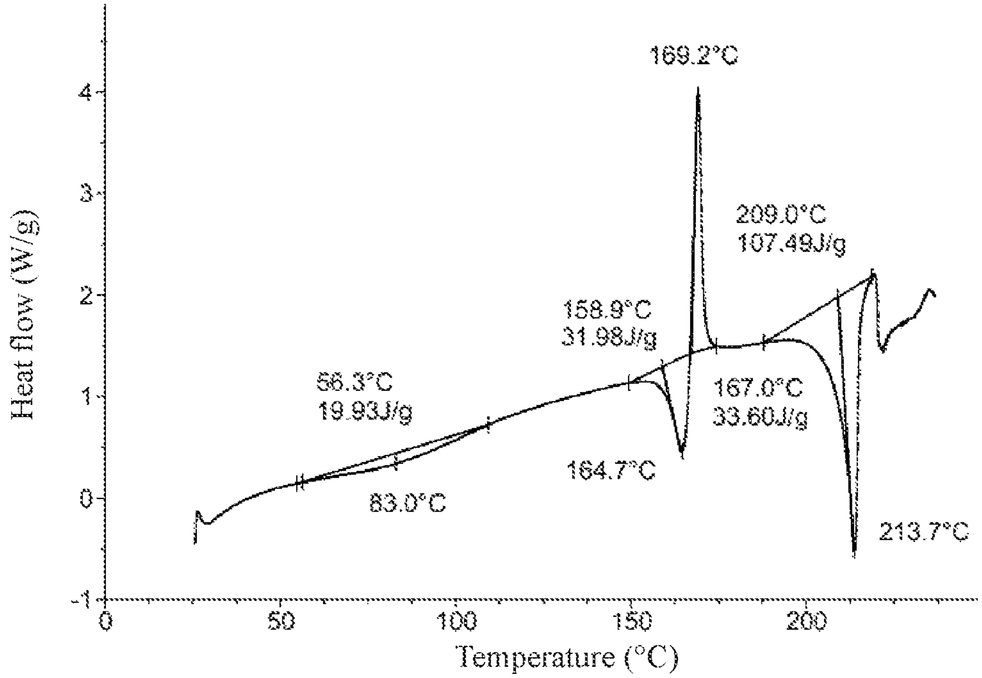
FIG. 17 is a DSC pattern of the crystalline form F of the compound 1.
Figure 18:
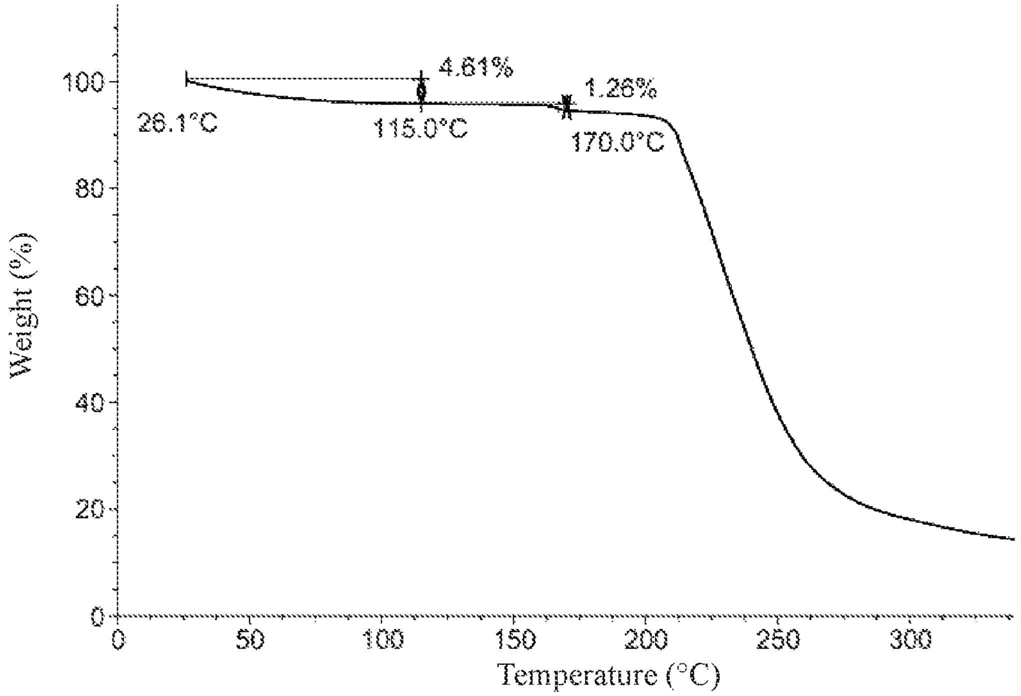
FIG. 18 is a TGA pattern of the crystalline form F of the compound 1.
Figure 19:
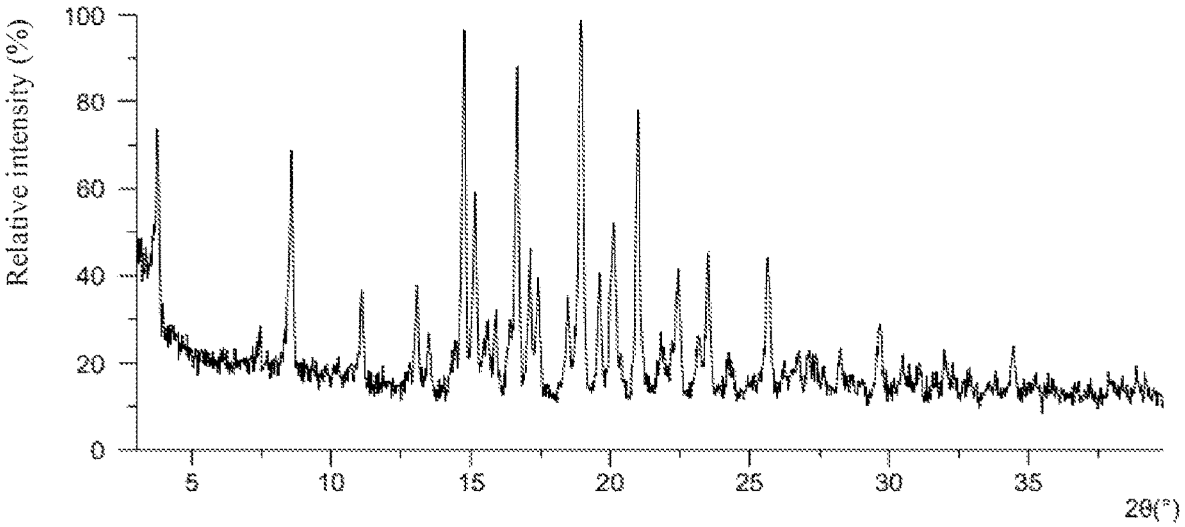
FIG. 19 is an XRPD pattern using Cu-Kα radiation of the crystalline form G of the compound 1.
Figure 20:
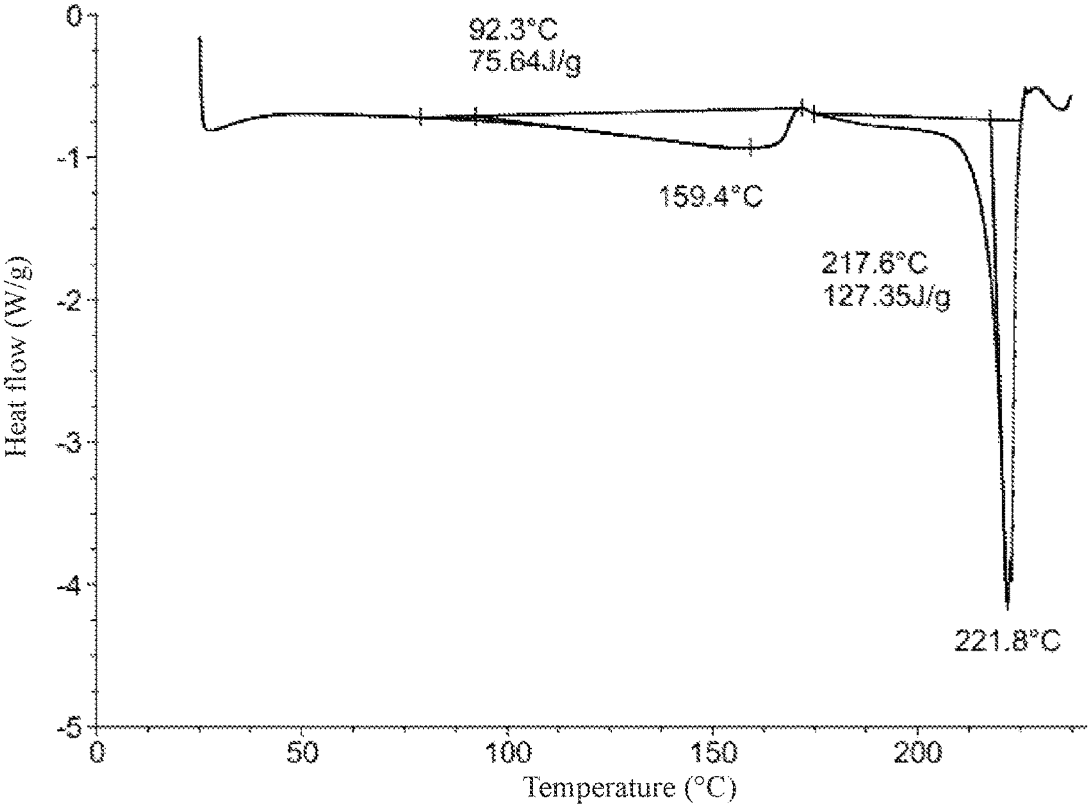
FIG. 20 is a DSC pattern of the crystalline form G of the compound 1.
Figure 21:
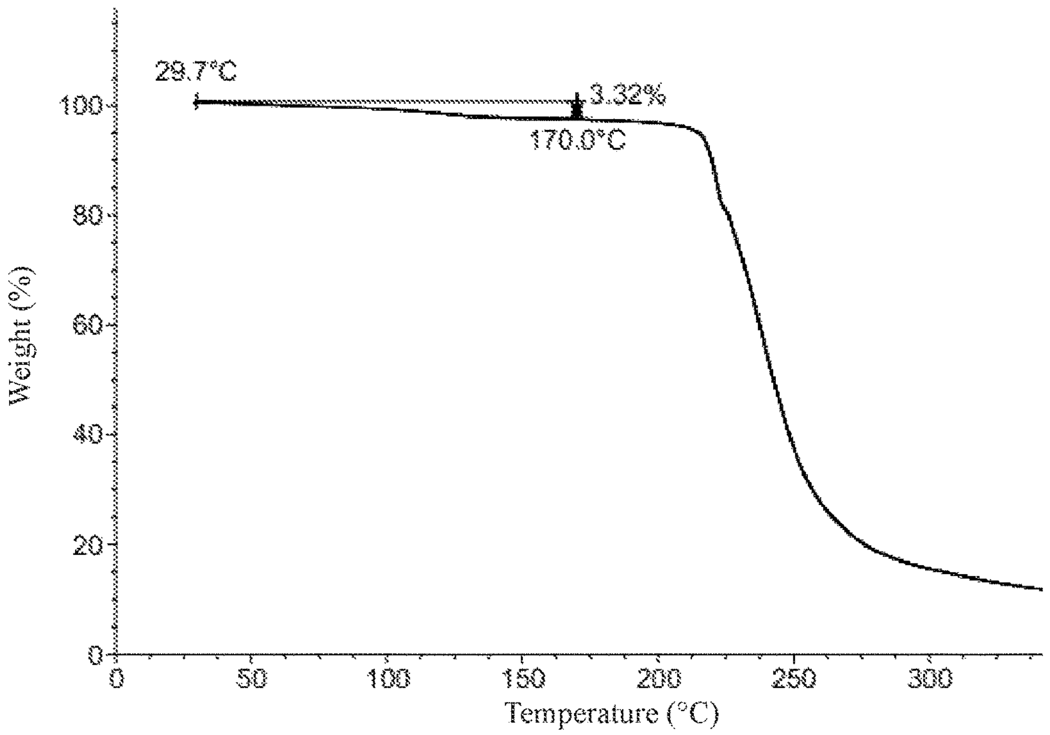
FIG. 21 is a TGA pattern of the crystalline form G of the compound 1.
Figure 22:
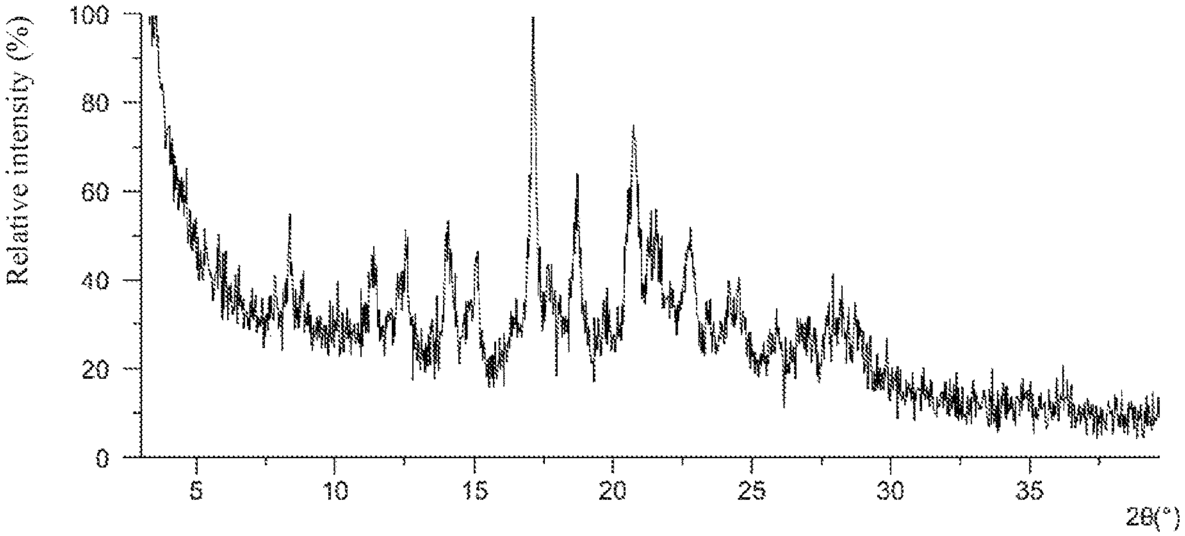
FIG. 22 is an XRPD pattern using Cu-Kα radiation of the crystalline form H of the compound 2.
Figure 23:
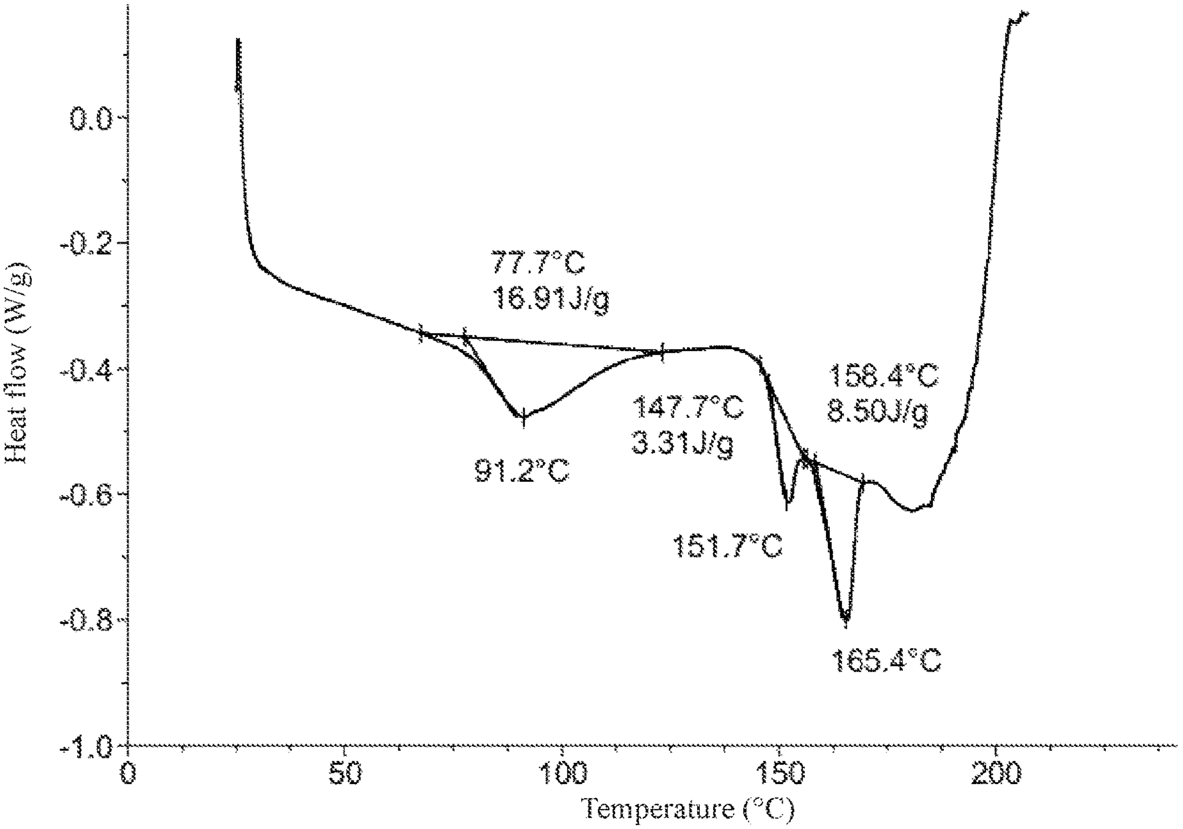
FIG. 23 is a DSC pattern of the crystalline form H of the compound 2.
Figure 24:
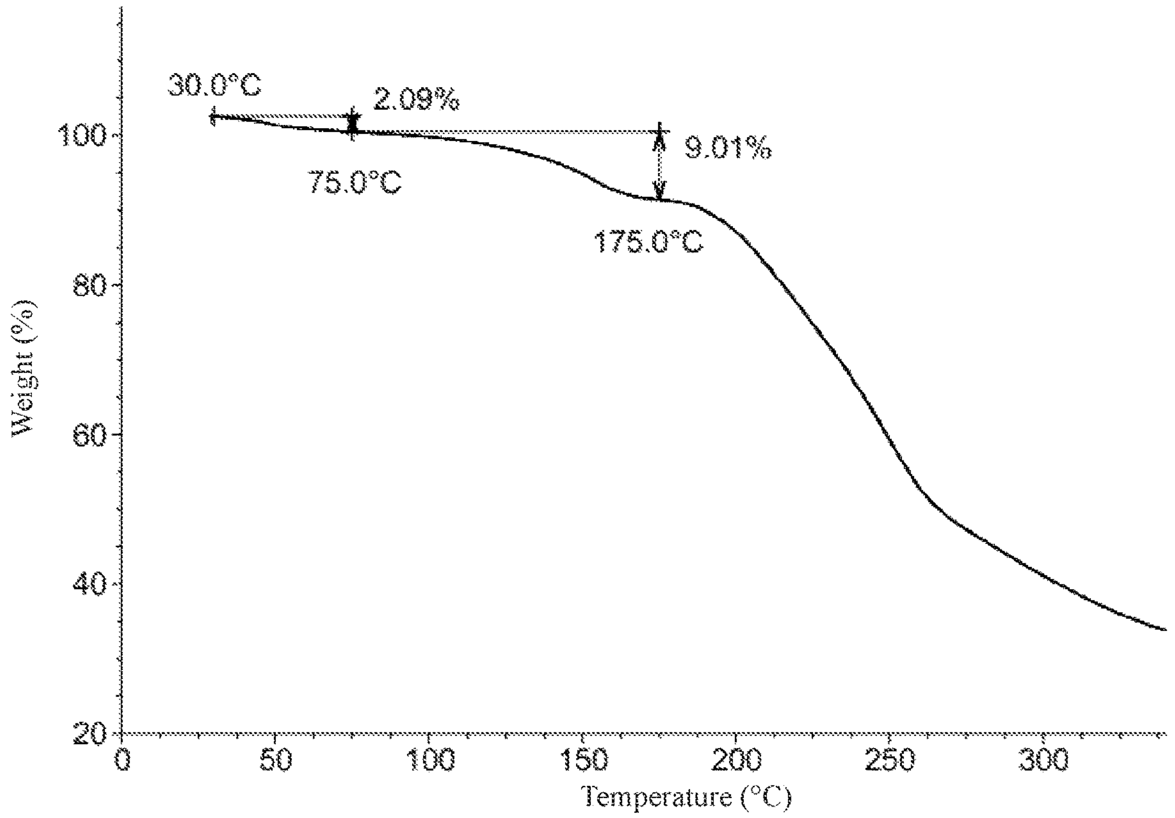
FIG. 24 is a TGA pattern of the crystalline form H of the compound 2.
Figure 25:
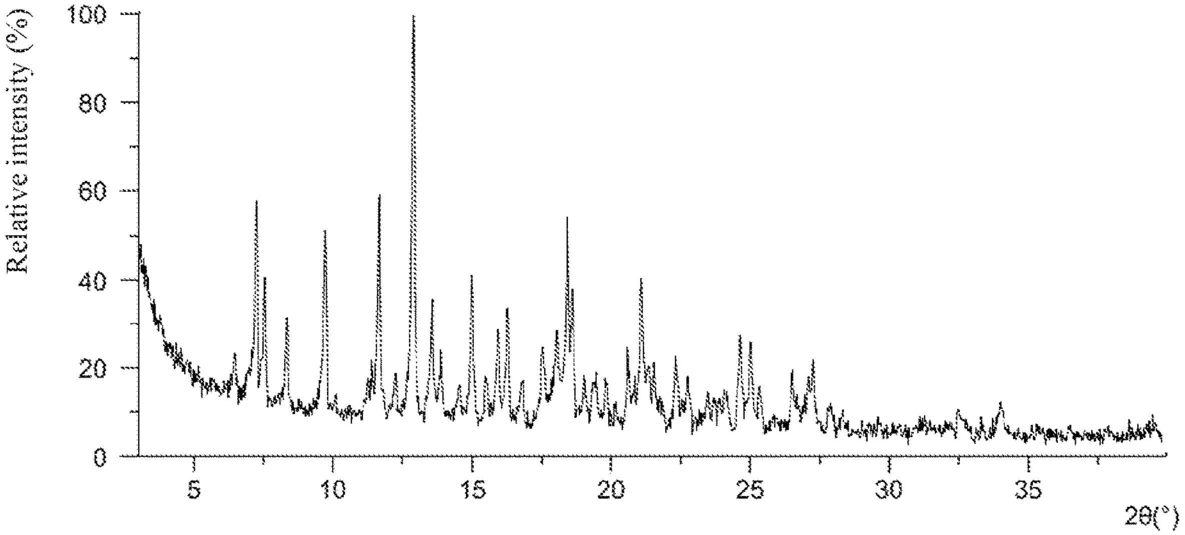
FIG. 25 is an XRPD pattern using Cu-Kα radiation of the crystalline form J of the compound 3.
Figure 26:
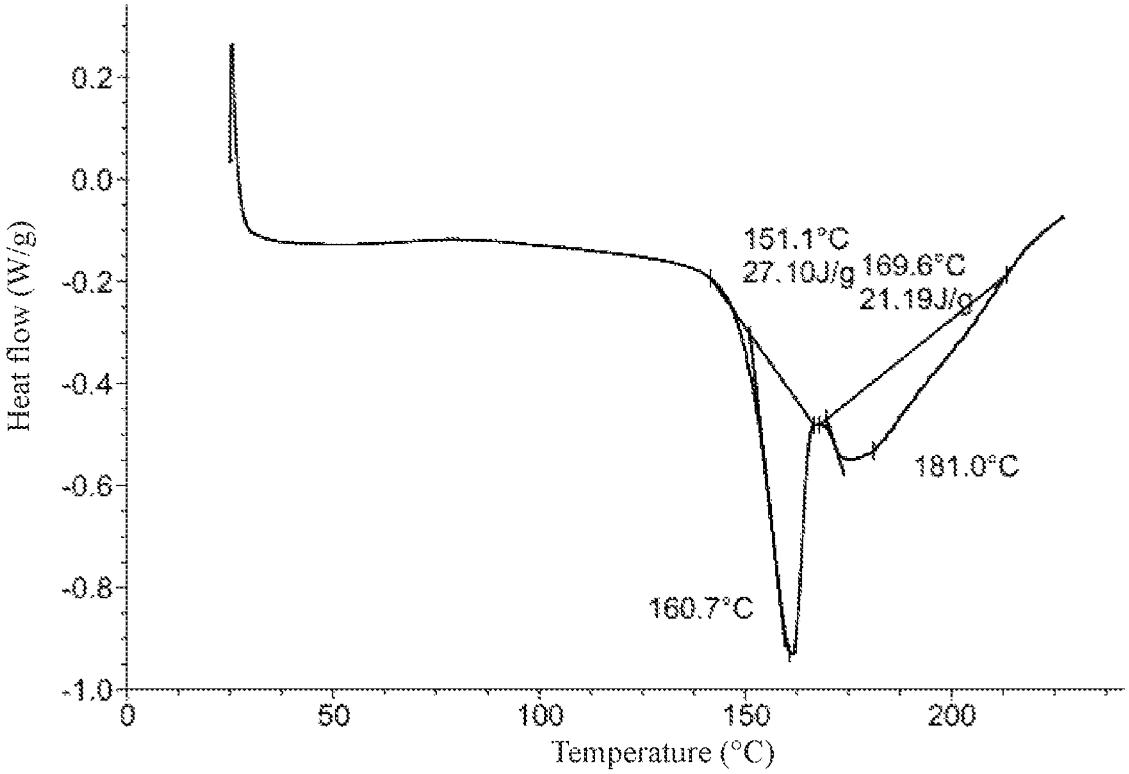
FIG. 26 is a DSC pattern of the crystalline form J of the compound 3.
Figure 27:
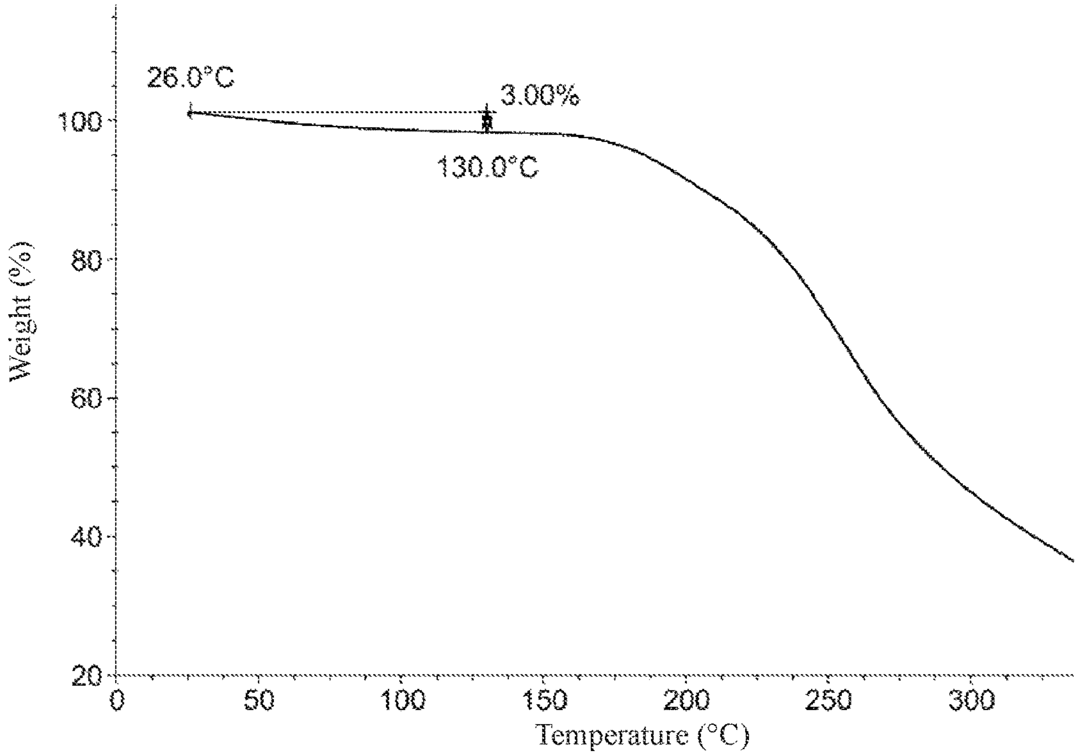
FIG. 27 is a TGA pattern of the crystalline form J of the compound 3.
Figure 28:
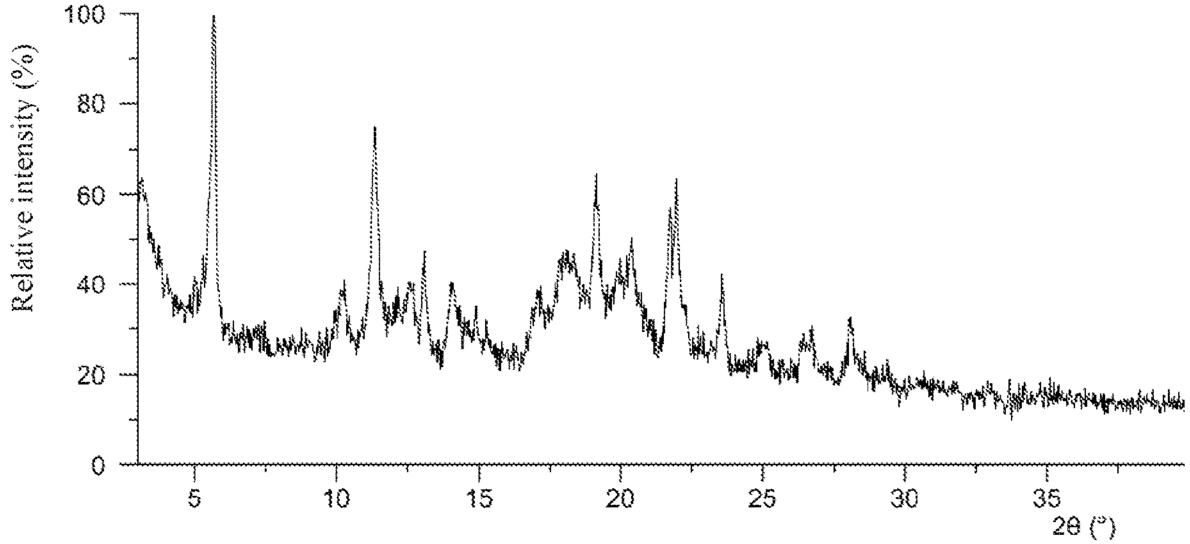
FIG. 28 is an XRPD pattern using Cu-Kα radiation of the crystalline form K of the compound 4.
Figure 29:
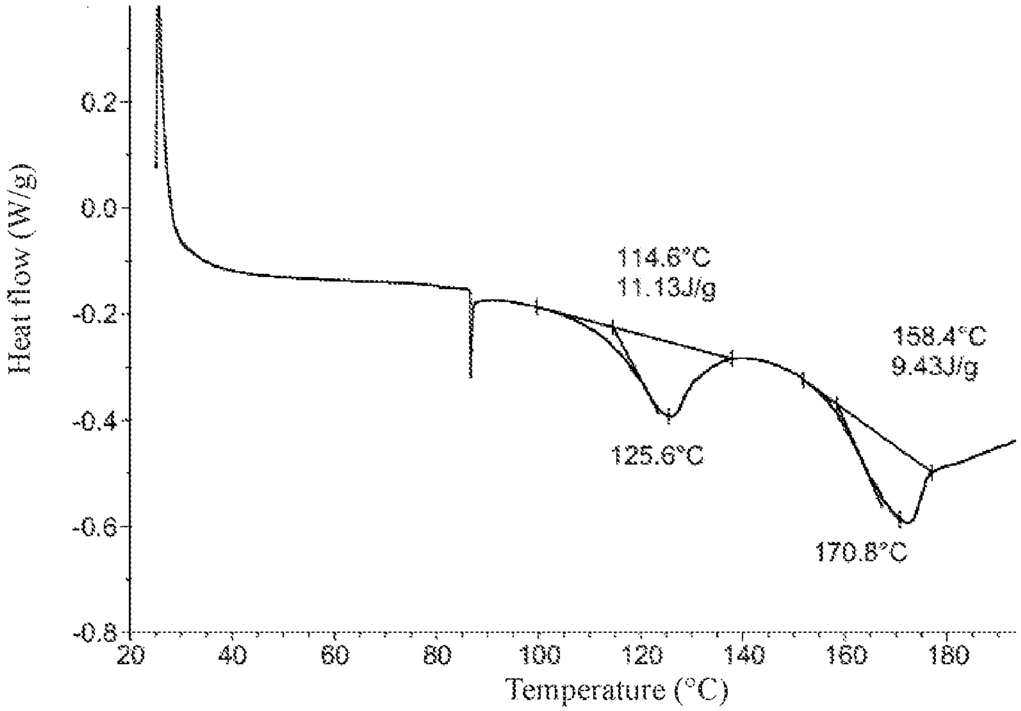
FIG. 29 is a DSC pattern of the crystalline form K of the compound 4.
Figure 30:
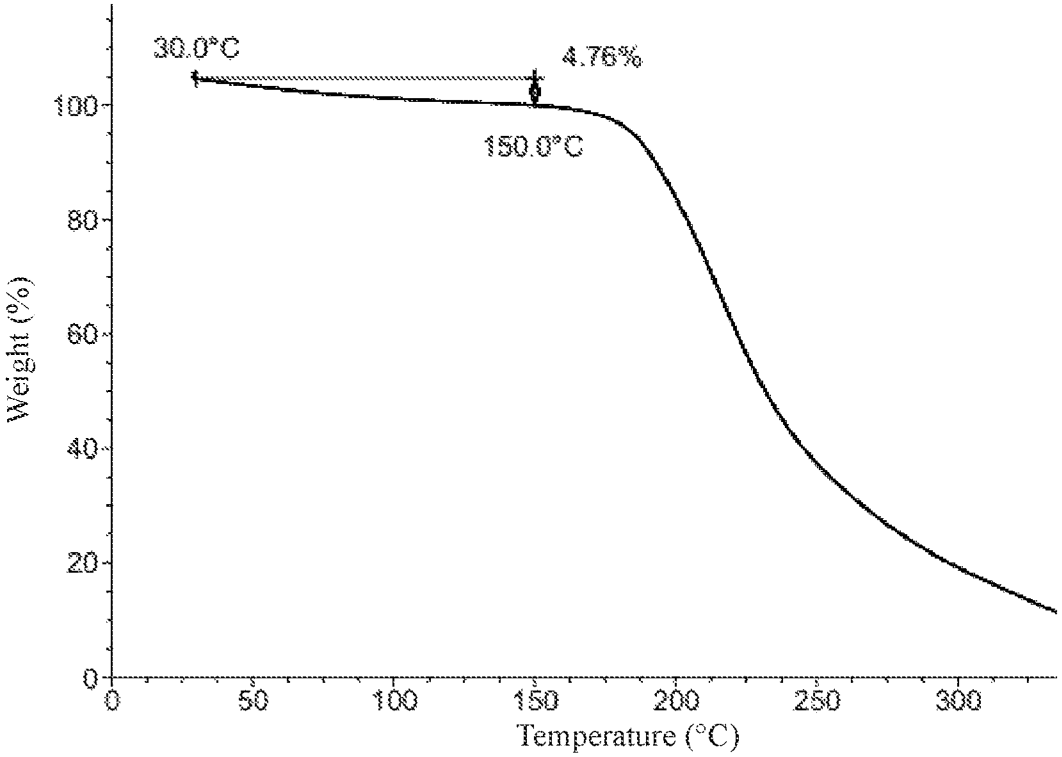
FIG. 30 is a TGA pattern of the crystalline form K of the compound 4.

Methodology: approximately samples of 10-20 mg were subjected to XRPD.

The detailed XRPD parameters were as follows:

Ray source: Cu, Kα (Kα1=1.540598 Å, Kα2=1.544426 Å, Kα2/Kα1 intensity ratio: 0.5)

X-ray tube voltage: 45 kV, current: 40 mA

Divergence slit: fixed, ⅛ deg

First soller slit: 0.04 rad, second soller slit: 0.04 rad

Receiving slit: none, anti-scatter slit: 7.5 mm

Measure time: 5 min

Angular range: 3-40 deg

Step width: 0.0263 deg

Step size: 46.665 s

Sample spinning speed: 15 rpm

Differential Scanning Calorimetry (DSC) Methodology of the Present Disclosure

Instrument: TA Q200/Q2000/2500 differential scanning calorimeter

Procedures: a sample (about 1-5 mg) was placed in a DSC aluminum pan and tested by heating the sample from 25° C. (room temperature) to just before decomposition at a heating rate of 10° C./min under a condition of 50 mL/min $N_2$.

Thermogravimetric Analysis (TGA) Methodology of the Present Disclosure

Instrument: TA Q5000/5500 thermogravimetric analyzer

Procedures: a sample (about 1-5 mg) was placed in a TGA aluminum pan and tested by heating the sample from room temperature to 350° C. at a heating rate of 10° C./min under a condition of 10 mL/min $N_2$.

DETAILED DESCRIPTION

In order to better understand the content of the present disclosure, further description is given with reference to specific examples, but the specific embodiments are not intended to limit the content of the present disclosure.

Example 1: Preparation of Compound 1

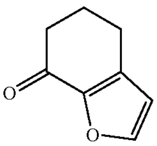

1a

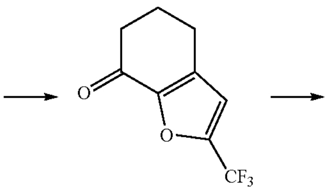

1b

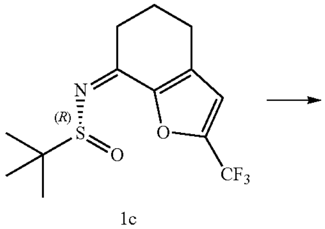

1c

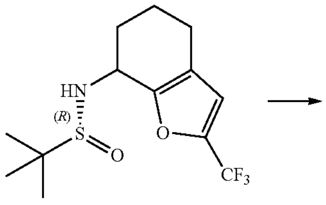

1d

-continued
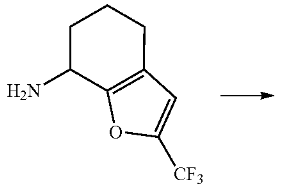
1e
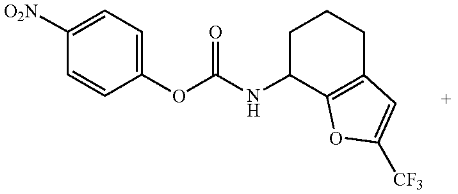
1f
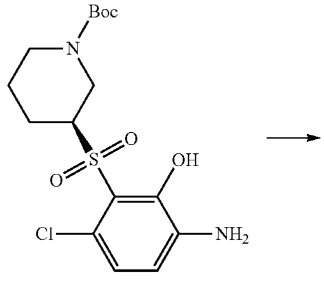
1g
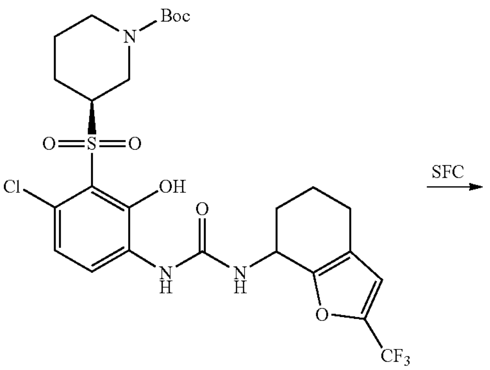
1h
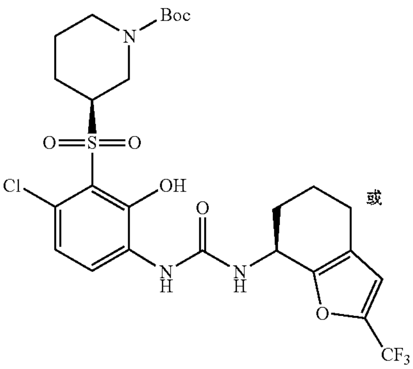
or
-continued
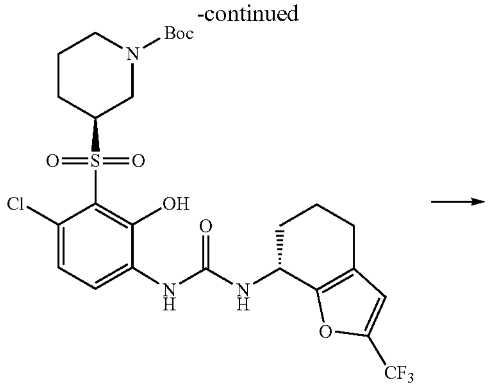
1i
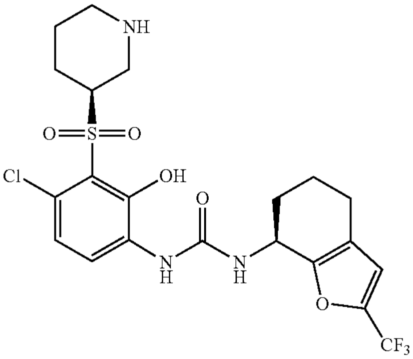
or
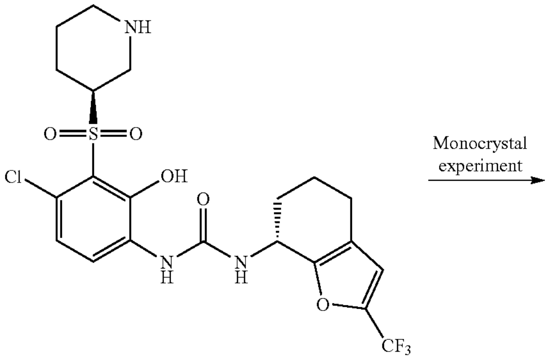
1
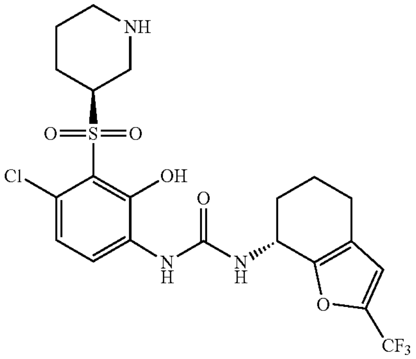
1
Step 1
Compound 1a (20.00 g, 146.90 mmol) was dissolved in 1,2-dichloroethane (300 mL), and 1-trifluoromethyl-1,2-benziodoxol-3(H)-one (51.06 g, 161.59 mmol) and copper (I) iodide (41.97 g, 220.35 mmol) were added. The reaction liquid was stirred at 60° C. for 14 h. The reaction liquid was filtered. The filtrate was stirred with saturated aqueous sodium bicarbonate solution (200 mL×2) and filtered. The filtrate was extracted with dichloromethane (100 mL×2). The organic phases were combined, washed with saturated brine (200 mL), dried over anhydrous sodium sulfate, filtered, and concentrated at reduced pressure. The residue was separated and purified by silica gel column chromatography (eluent: petroleum ether/ethyl acetate, 100:1-5:1) to give compound 1b.

$^1$H NMR (400 MHz, $CDCl_3$) δ: 6.80 (s, 1H), 2.83-2.79 (m, 2H), 2.65-2.61 (m, 2H), 2.24-2.17 (m, 2H).

Step 2

Compound 1b (8.50 g, 41.64 mmol) was dissolved in anhydrous toluene (150 mL), and (R)-(−)-2-methyl-2-propanesulfinamide (7.57 g, 62.46 mmol) and tetraethyl titanate (28.49 g, 124.91 mmol) were added. The reaction liquid was stirred at 90° C. for 3 h. To the reaction liquid were added water (100 mL) and ethyl acetate (100 mL). The mixture was homogenously stirred and filtered, and the filtrate was extracted with ethyl acetate (60 mL×2). The organic phases were combined, washed with saturated brine (100 mL), dried over anhydrous sodium sulfate, filtered, and concentrated at reduced pressure. The residue was separated and purified by silica gel column chromatography (eluent: petroleum ether/ethyl acetate, 10:1-1:1) to give compound 1c.

By MS-ESI, $[M+H]^+$ calculated 308, found 308.

Step 3

Compound 1c (8.30 g, 27.01 mmol) was dissolved in tetrahydrofuran (150 mL) and a solution of diisobutylaluminum hydride in toluene (1 M, 41 mL, 40.5 mmol) was slowly added dropwise at 0° C. under nitrogen atmosphere. The reaction liquid was stirred at 0° C. for 1 h. Water (200 mL) was added to the reaction liquid to quench the reaction. The mixture was homogenously stirred and filtered, and the filtrate was extracted with ethyl acetate (100 mL×2). The organic phases were combined, washed with saturated brine (100 mL), dried over anhydrous sodium sulfate, filtered, and concentrated at reduced pressure. The residue was separated and purified by silica gel column chromatography (eluent: petroleum ether/ethyl acetate, 10:1-1:1) to give compound 1d.

By MS-ESI, the calculated [M+H]+ calculated 310, found 310.

Step 4

Compound 1d (6.20 g, 20.04 mmol) was dissolved in anhydrous tetrahydrofuran (60 mL) and concentrated hydrochloric acid (8 mL, 12 N) was added dropwise at 0° C. The reaction liquid was stirred at 0° C. for 1 h. The reaction liquid was adjusted to pH=8-9 with aqueous solution of solid sodium carbonate and filtered. The filtrate was concentrated at reduced pressure, and the residue was added with water (30 mL) and extracted with dichloromethane (40 mL×2). The organic phases were combined, washed with saturated brine (100 mL), dried over anhydrous sodium sulfate, filtered, and concentrated at reduced pressure. The residue was separated and purified by silica gel column chromatography (eluent: dichloromethane/methanol, 100:1-10:1) to give compound 1e.

$^1$H NMR (400 MHz, $CDCl_3$) δ: 6.58 (s, 1H), 3.40-3.98 (m, 1H), 2.47-2.41 (m, 2H), 2.15-2.11 (m, 1H), 1.89-1.86 (m, 1H), 1.74-1.65 (m, 2H).

Step 5

Compound 1e (300 mg, 1.46 mmol) was dissolved in dichloromethane (10 mL), and sodium carbonate (232.46 mg, 2.19 mmol) and 4-nitrobenzyl chloroformate (265.25 mg, 1.32 mmol) were added. The reaction liquid was stirred at 20° C. for 1 h. After the reaction, the reaction liquid was diluted with dichloromethane (40 mL) and washed with water (50 mL). The organic phase was washed with saturated brine (50 mL), dried over anhydrous sodium sulfate, filtered and concentrated at reduced pressure to dryness to give a crude product. The crude product was separated and purified by flash preparative chromatography (eluent: ethyl acetate/petroleum ether=0-20%) to give intermediate compound 1f.

Step 6

Compound 1g (225 mg, 575.62 μmol) was dissolved in dichloromethane (10 mL). Triethylamine (174.74 mg, 1.73 mmol) and intermediate compound 1f (333.47 mg, 690.75 μmol) were added. The mixture was stirred at 10-20° C. for 16 h. After the reaction, the reaction liquid was diluted with dichloromethane (40 mL) and washed with water (50 mL). The organic phase was washed with saturated brine (50 mL×2), dried over anhydrous sodium sulfate, filtered and concentrated at reduced pressure to dryness to give a crude product. The crude product was separated and purified by flash preparative chromatography (eluent: ethyl acetate/petroleum ether=1/0-2/1) to give compound 1h.

By MS-ESI, $[M+H]^+$ calculated 622, $[M+Na]^+$ found 644.1.

Step 7

Compound 1h (460 mg, 739.49 μmol) was separated by supercritical fluid chromatography (separation conditions: column: DAICEL CHIRALPAK AS-H 250 mm×30 mm, 5 μm; mobile phase, A: carbon dioxide, B: ethanol (0.1% aqueous ammonia); gradient, B %: 25%-25%) to give chiral isomer compound 1i with a retention time of 3.045 min (the second peak).

Analysis conditions: column: ChiralPak AS-3 150×4.6 mm I.D., 3 μm; mobile phase, A: carbon dioxide, B: ethanol (0.05% diethylamine); gradient, mobile phase B was elevated from 5% to 40% in 5 min, reduced from 40% to 5% in 0.5 min, and maintained at 5% for 1.5 min; flow rate: 2.5 mL/min; column temperature: 35° C.; wavelength: 220 nm Step 8

Compound 1i (305 mg, 490.31 μmol) was dissolved in ethyl acetate (5 mL), and ethyl acetate hydrochloride (4 M, 6.13 mL) was added. The reaction liquid was stirred at 20° C. for 1 h. After the reaction, the reaction liquid was directly concentrated to dryness at reduced pressure. The residue was dissolved in dichloromethane and saturated sodium bicarbonate solution was added to adjust the pH to 7-8. The organic phase was washed with saturated brine (10 mL), dried over anhydrous sodium sulfate, filtered and concentrated at reduced pressure to dryness to give a crude product. The crude product was purified with acetonitrile (2 mL) to give compound 1.

$^{1}H$ NMR (400 MHz, METHANOL-d4) δ: 7.91 (d, J=8.4 Hz, 1H), 6.76 (s, 1H), 6.53 (d, J=8.4 Hz, 1H), 4.94 (br s, 1H), 4.41 (br s, 1H), 3.72 (br d, J=10.8 Hz, 1H), 3.21-3.05 (m, 2H), 2.88-2.76 (m, 1H), 2.57-2.39 (m, 2H), 2.09-1.95 (m, 2H), 1.94-1.78 (m, 6H).

By MS-ESI, $[M+H]^+$ calculated 522, found 522.0.

Step 9: Preparation of Monocrystal of Compound 1 and Determination of Absolute Configuration The culture procedure of monocrystal of compound 1: about 5 mg of sample was placed in a 2-mL brown sample vial, and 200 μL of acetone was added. A colorless rectangular columnar crystal was generated after 5 days. The crystal for diffraction had dimensions of 0.06×0.12×0.14 mm. The crystal is a triclinic system with a space group of P1 and the following unit cell parameters: a=10.6397(7), b=11.7976(8), c=12.0726(8) Å, α=79.751(3), β=70.745(3), γ=84.453(3)°, the volume of unit cell V=1406.61(16) $Å^3$. The number of asymmetric units in the unit cell Z=1. Diffraction intensity data were collected using a Bruker D8 venture diffractometer using CuKα radiation and φ/ω scanning mode. A total of 15938 diffraction points were collected, including 9049 independent diffraction points and 6590 observable points (I/sigma≥2).

The crystal structure was analyzed using a direct method (Shelxs97), give positions of all 70 non-hydrogen atoms. The structure parameters were corrected, and the atoms were identified using least squares. Positions of all hydrogen atom were obtained using geometric calculation and difference Fourier method. After fine correction, R1=0.1052, wR2=0.2914 (w=1/σ|F|2) and S=1.050.

The monocrystal experiment showed that the molecular alignment in the crystalline state belongs to the first type of space group, the compound should have optical activity, and the Flack coefficient is 0.129(14). Thus the absolute configuration of the compound in the crystal was determined. In the crystalline state, hydrogen bonds were observed between molecules. The stable spatial alignment of molecules is maintained by van der Waals interaction and hydrogen bonds therebetween.

Figure 34:
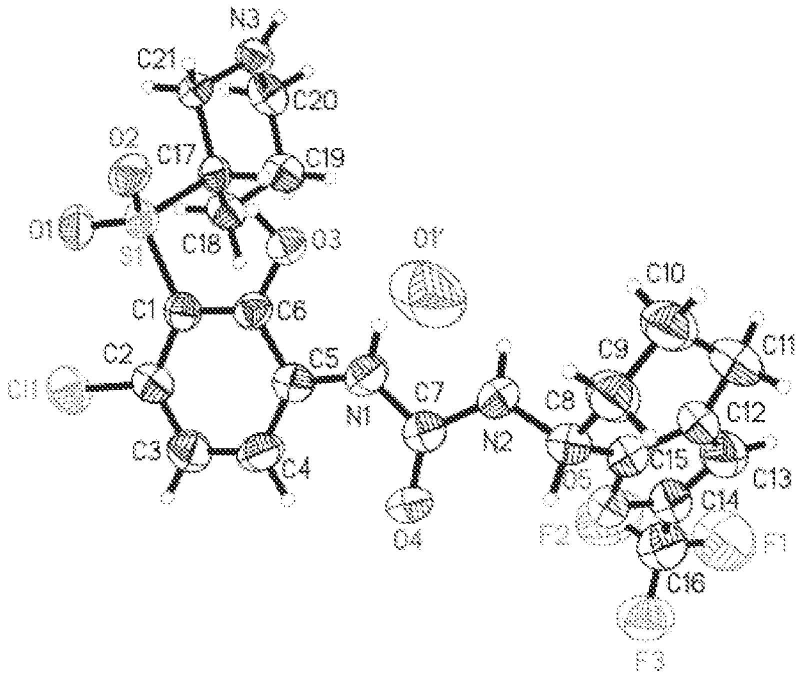
FIG. 34 is an ellipsoid plot of the three-dimensional structure of the compound 1 molecule.
Figure 35:
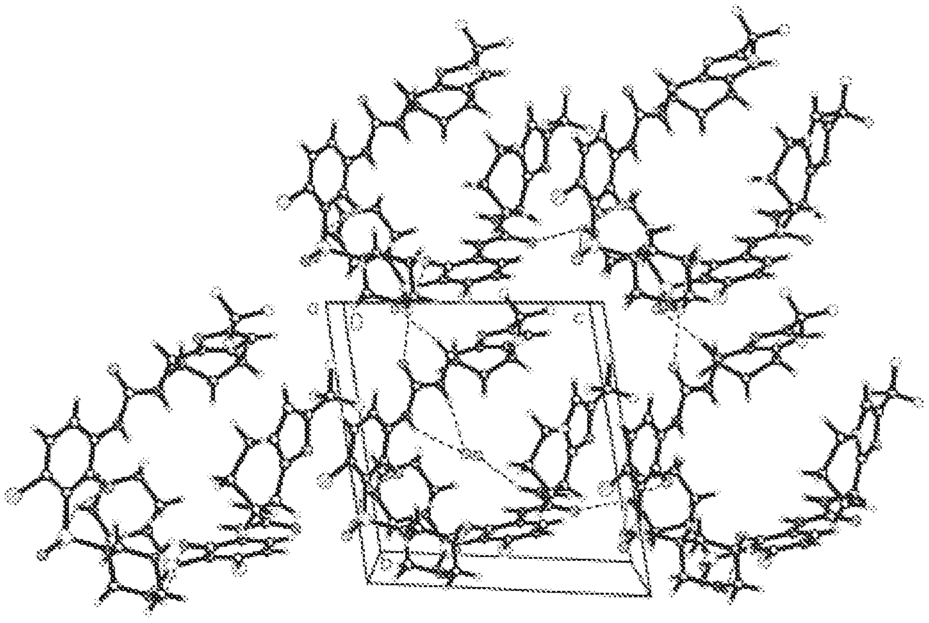
FIG. 35 is a crystal packing diagram along the a-axis.

The results are shown in FIGS. 34 and 35, which are the ellipsoid plot of the three-dimensional structure of compound 1 molecule and the crystal packing diagram along the a-axis, respectively.

Example 2: Preparation of Crystalline Form A of Compound 1

Compound 1 (1.4 g) was slurried with methanol (10 mL)/water (5 mL) at 60° C. for 2 h. The mixture was cooled to 20° C., stirred for 1 h and filtered under vacuum to give a white solid. The white solid was dried under vacuum at 50° C. for 18 h. The crystalline form of the pure product is crystalline form A.

Experimental Example 3: Screening of Crystalline Forms of Compound 1

Various crystalline forms of free compound 1 molecule were obtained under the following conditions:

Crystalline form B: About 15 mg of compound 1 was added into an HPLC vial, and 0.2 mL of ethyl acetate was added to the vial. The mixture was suspended and stirred at room temperature for about two days and centrifuged to give crystalline form B.

Crystalline form C: About 15 mg of compound 1 was added into an HPLC vial, and 0.2 mL acetonitrile was added to the vial. The mixture was suspended and stirred at room temperature for about three days and centrifuged to give a solid. The resulting solid was dried under vacuum at 50° C. for 2 h to give crystalline form C.

Crystalline form D: About 15 mg of compound 1 was added into an HPLC vial, and 0.2 mL tetrahydrofuran/water (19:1, v:v) was added to the vial. The mixture was suspended and stirred at room temperature for about three days to give a clear solution. The solution was stirred at −20° C. for about 1 day and centrifuged to give a solid. The resulting solid was dried under vacuum at 50° C. for 2 h to give crystalline form D.

Crystalline form E: About 15 mg of compound 1 was added into an HPLC vial, and 0.2 mL of acetonitrile was added to the vial. The mixture was suspended, stirred at room temperature for about two days and centrifuged to give crystalline form E.

Crystalline form F: About 15 mg of compound 1 was added into an HPLC vial, and 0.2 mL acetonitrile was added to the vial. The mixture was suspended and stirred at room temperature for about two days and centrifuged to give a solid. The solid was dried under vacuum at 50° C. for 2 h to give crystalline form F.

Crystalline form G: About 40 mg of compound 1 was added into a solvent of ethanol/water (0.28 mL/0.12 mL) at a final concentration of 100 mg/mL. The solution was stirred at 20° C. for 4 days and centrifuged to give a precipitate. The precipitate was dried under vacuum at 50° C. for 16 h to give crystalline form G.

Experimental Example 4: Screening of Crystalline Forms of Salts of Compound 1

Various crystalline forms of salts of compound 1 were obtained under the following conditions:

Crystalline form K: About 15 mg of compound 1 was dissolved in 0.2 mL of ethyl acetate in an HPLC vial before about 5.3 mg of hippuric acid was added to the vial. The mixture was suspended and stirred at room temperature for about five days and centrifuged to give a solid. The resulting solid was dried under vacuum at 50° C. for 2 h to give crystalline form K of compound 4. The molar ratio of the free crystalline form to the acid portion was: 1:0.95.

Crystalline form H: About 15 mg of compound 1 was dissolved in 0.2 mL of acetonitrile in an HPLC vial before 2.14 μL of concentrated phosphoric acid (15 M) was added to the vial. The mixture was suspended and stirred at room temperature for about five days and centrifuged to give a solid. The resulting solid was dried under vacuum at 50° C. for 2 h to give crystalline form H of compound 2. The molar ratio of the free crystalline form to the acid portion was: 1:0.91.

Crystalline form J: About 15 mg of compound 1 was dissolved in 0.2 mL of acetonitrile in an HPLC vial before about 3.5 mg of maleic acid was added to the vial. The mixture was suspended and stirred at room temperature for about five days and centrifuged to give a solid. The resulting solid was dried under vacuum at 50° C. for 2 h to give crystalline form J of compound 3. The molar ratio of the free crystalline form to the acid portion was: 1:0.98.

Experimental Example 5: Stability Assay of Solid Crystalline Form A in Conditions of High Temperature, High Humidity, High Temperature and High Humidity, and Illumination 6 replicate samples of crystalline form A each of about 20-30 mg were placed in HPLC vials and evenly spread at the bottom as a thin layer. The samples were placed in conditions of high temperature (60° C.), high humidity (92.5% humidity, 25° C.), high temperature and high humidity (60° C./75% humidity), and under illumination (including in the dark as control) for stability assay. For samples in a 60° C./75% thermostatic incubator and a 92.5% RH desiccator, the vials were sealed using films. On the films 5 small holes were provided to ensure that the sample was in sufficient contact with atmospheric air. For samples at 60° C., under illumination and in the dark, the vials were tightly capped (for the sample in the dark the vial was wrapped with tin foil). The samples were tested on day 10 for high humidity (92.5% humidity) condition, on days 5 and 10 for high temperature (60° C.) condition, on days 10 and 30 for high temperature and high humidity (60° C./75% humidity) condition, and on day 10 for illumination condition. All test results were compared with the corresponding initial test results on day 0, as shown in the following Tables 11, 12, 13 and 14:

TABLE 11

Stability assay of solid crystalline form A at high temperature (60° C.)

| Time point (day) | Appearance | Crystalline form |
|---|---|---|
| 0 | White powder | Crystalline form A |
| 5 | White powder | Crystalline form A |
| 10 | White powder | Crystalline form A |

TABLE 12

Stability assay of solid crystalline form A at high humidity (92.5% humidity, 25° C.)

| Time point (day) | Appearance | Crystalline form |
|---|---|---|
| 0 | White powder | Crystalline form A |
| 10 | White powder | Crystalline form A |

TABLE 13

Stability assay of solid crystalline form A at high temperature and high humidity (60° C./75% humidity)

| Time point (day) | Appearance | Crystalline form |
|---|---|---|
| 0 | White powder | Crystalline form A |
| 10 | White powder | Crystalline form A |
| 30 | White powder | Crystalline form A |

TABLE 14

Stability assay of solid crystalline form A under illumination

| Time point (day) | Appearance | Crystalline form |
|---|---|---|
| In the dark for 10 days | White powder | Crystalline form A |
| Under illumination for 10 days | White powder | Crystalline form A |

Conclusion: The crystalline form A of compound 1 of the present disclosure has good stability and druggability.

Experimental Example 6: Crystalline Form Stability Assay of Crystalline Form A of Compound 1—Solvent Water Activity The crystalline form A of compound 1 was stirred in the corresponding solvents (100 mg/mL) at 20° C. for 4 days. The solutions were centrifuged to give precipitates, and the precipitates were dried under vacuum at 50° C. and subjected to XRPD. The results are shown in Table 15 below:

TABLE 15

Crystalline form stability assay of crystalline form A - solvent water activity

| No. | Solvent | Crystalline form |
|---|---|---|
| 1 | Methanol | Crystalline form A |
| 2 | Ethanol | Crystalline form A |
| 3 | Methanol/water = 1/1.5 | Crystalline form A |
| 4 | Water | Crystalline form A |

It can be seen from the table above that the crystalline form A of compound 1 is stable in the above solvents.

Experimental Example 7: In Vitro Assay of the Compound

CXCR2 β-arrestin cells (DiscoverX) of PathHunter® were cultured in standard conditions and inoculated at 20 μL/well to a 384-well white microplate. Before testing, the cells were incubated at 37° C. for an appropriate period of time. The test compound was serially 3-fold diluted in DMSO to give 8 concentrations. Shortly before testing, the serially diluted test samples were further diluted with test buffer to 5 folds of the test concentration. 5 μL of further diluted test samples were added to the cells and the cells were incubated at 37° C. for 30 min. The concentration of vehicle was 1%. 5 μL of 6×EC80 agonist (CXCL8) buffer was then added to the cells, and the cells were incubated at 37° C. for 90 min. The test signal was generated by adding 15 μL (50% v/v) of PathHunter detection mixture reagent in one portion and subsequently incubating the cells for 1 h. The chemiluminescence signal of the microplate was read by a PerkinElmer Envision™ instrument. The biological activities of the test compounds were analyzed by CBIS data analysis kit (ChemInnovation, CA), shown as $IC_{50}$ values. The experimental results are shown in Table 16:

TABLE 16

| Results of in vitro activity test for compound of the present disclosure | |
|---|---|
| Compound | $IC_{50}$ |
| Compound 1 | 22 nM |

Conclusion: Compound 1 has a potent antagonism against the CXCR2 receptor.

Experimental Example 8: Pharmacokinetic Evaluation of Compound 1

In this plasma pharmacokinetic assay, 4 male Lewis rats were used and randomized into two groups, with 2 animals in each group. The animals in the first group were given 2 mg/kg of the test compound by intravenous injection and the animals in the second group were given 10 mg/kg of the test compound by intragastric administration. An aqueous solution of 1% DMSO/20% PEG400/79% (HP-b-CD) was used as the vehicle, and the resulting intravenous and intragastric formulations (adjusted to pH=2.78) were clear solutions. Blood samples were collected from saphenous veins of animals at 0.0830, 0.25, 0.5, 1, 2, 4, 6, 8 and 24 hours post-dose for the intravenous injection group, and at 0.25, 0.5, 1, 2, 4, 6, 8 and 24 hours post-dose for the intragastric administration group, with 3 samples at each time point. Plasma samples of the intragastric administration group were cryopreserved at −80° C. and thawed before LC-MS/MS sample analysis. Acetonitrile containing internal standard was added to the thawed plasma samples at a certain ratio to precipitate proteins.

The mixture was centrifuged, and the supernatant was subjected to analysis by LC-MS/MS. An API4000 or 5500 system equipped with ACQUITY UPLC BEH C18 (2.1×50 mm, 1.7 μm) column and ESI positive or negative ion source was used. Each analysis batch included standard samples with 8 concentrations. A curve of the ratio of the peak areas of the test compound to the internal standard (IS) vs. the concentration of the test compound in the plasma sample was plotted, and linear regression was performed using $1/X^2$ as weighting coefficient to give a regression equation between the measured response and the concentration. Each analysis batch also included corresponding quality control samples. Data processing was performed using Phoenix 6.3 WinNonlin® to give corresponding PK parameters. The experimental results are shown in Table 17.

TABLE 17

| Results of pharmacokinetic assay | | | | |
|---|---|---|---|---|
| | Intravenous injection Clearance (CL, mL/min/kg) | Intragastric administration Half life ($T_{1/2}$, h) | Intragastric administration Maximum plasma concentration ($C_{max}$, nM) | Intragastric administration Plasma exposure (AUC, nM · hr) |
| Compound 1 | 5.07 | 4.22 | 3005 | 31349 |

Conclusion: Compound 1 has good pharmacokinetic properties in rats.

Experimental Example 9: Therapeutic Effect of the Compound on PPE-Induced COPD Model Objective:

To test the therapeutic effect of the compound on PPE-induced SD rat COPD model.

Materials:

Animals: SD rats (male, 160-180 g, 6 weeks age)

Test compounds: porcine pancreatic elastase (Sigma, 0.068 U/μL); Danirixin, compound 1.

Grouping: 1) vehicle group

2) COPD model group (porcine pancreatic elastase modeling group/solvent group)

3) PPE+Danirixin (30 mpk)

4) PPE+compound 1 (10 mpk)

5) PPE+compound 1 (30 mpk)

Procedures:

1. Modeling: PPE was given retrolingually.
2. Administration: an aqueous solution of 1% DMSO/20% PEG400/79% (HP-b-CD) was used as the vehicle, and the drugs were administrated intragastrically everyday at a volume of 2 mL/rat for 4 weeks.
3. Endpoint: On day 29, pulmonary function test, sample collection, and inflammatory cell count in bronchoalveolar lavage fluid.

Figure 31:
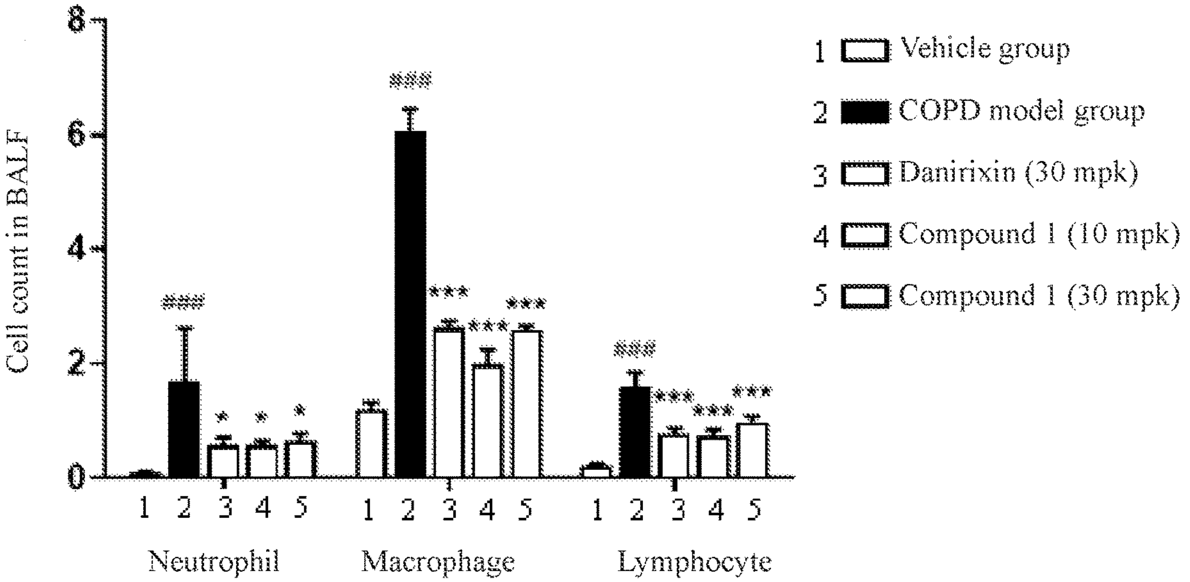
FIG. 31 illustrates the relationship between differential counts of various immune cells in lung tissues and doses of compounds in various animal groups; note: ###p<0.001 vs. vehicle group; *p<0.05 vs. model group; ***p<0.001 vs. model group.
Figure 32:
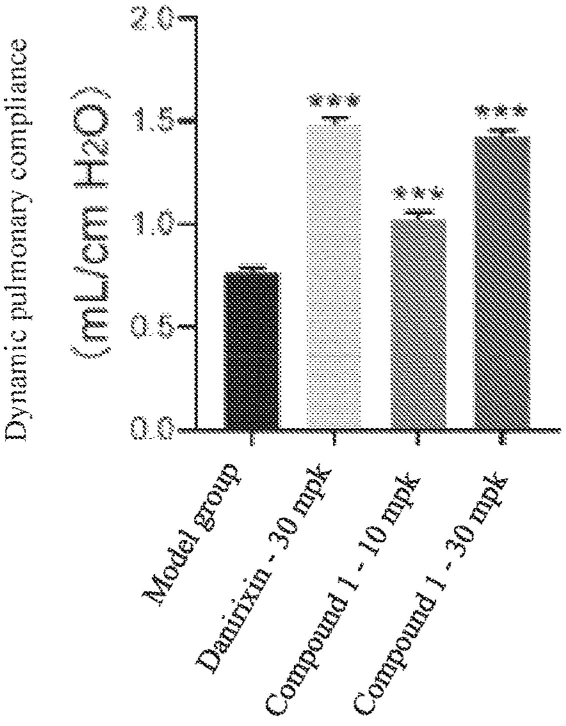
FIG. 32 shows the relationship between dynamic pulmonary compliance and doses of compounds in various animal groups; note: ***p<0.001 vs. model group.
Figure 33:
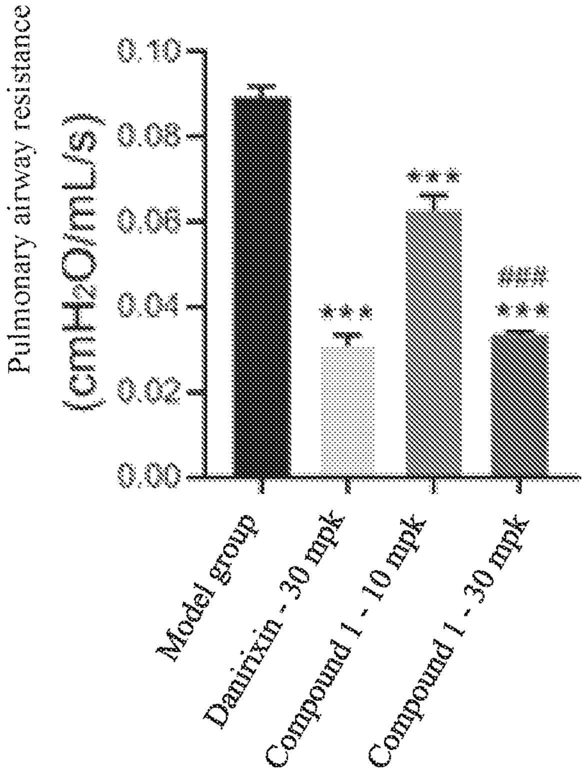
FIG. 33 shows the relationship between pulmonary airway resistance and doses of compounds in various animal groups; note: ***p<0.001 vs. model group; ###p<0.001 vs. compound 1-10 mpk group.

Bronchoalveolar lavage: The rats were sacrificed, and dissected at the neck. Trachea intubation was performed. 1 mL of cold sulfate buffer at 4° C. was infused for 3 lavages, and the lavage fluids were combined. The combined lavage fluids were centrifuged at 1200 rpm/min for 5 min, and the supernatant was discarded. The cell suspension was collected;

The results of the experimental data are shown in FIGS. 31,32 and 33;

Conclusion: In the PPE-induced rat COPD model, the compound 1 of the present disclosure and Danirixin at high dose (30 mpk) significantly reduced the count of immune inflammatory cells such as neutrophils, macrophages and lymphocytes and the like in bronchoalveolar lavage fluid, showing good inhibitory effect on inflammation. At the same time, the compound of the present disclosure also demonstrated comparable anti-inflammatory effect at low dose (10 mpk). Pulmonary function, as the "gold standard" for the diagnosis of chronic obstructive pulmonary disease, was significantly improved by compound 1 of the present disclosure at low dose (10 mpk).

Experimental Example 10: Pharmacodynamic Evaluation of Crystalline Form A of Compound 1 for Anti-Inflammation Effect in Rat COPD Model Induced by Smoking Combined with Lipopolysaccharide Objective:

To test the early anti-inflammatory effect of crystalline form A of compound 1 in rat COPD model induced by smoking combined with lipopolysaccharide (LPS).

Materials:

Animals: SD rats (male, 180-220 g, 8-10 weeks age)

Modeling agents and test compounds: lipopolysaccharide (LPS) (Sigma), cigarettes (commercially available Marlboro cigarettes); Danirixin, crystalline form A of compound 1.

Grouping: 1) vehicle group

2) COPD model group (smoking+LPS modeling group/solvent group)

3) smoking+LPS+Danirixin (30 mpk)

4) smoking+LPS+crystalline form A of compound 1 (3 mpk)

5) smoking+LPS+crystalline form A of compound 1 (10 mpk)

6) smoking+LPS+crystalline form A of compound 1 (30 mpk)

Procedures:

1. Modeling: the animal model was prepared by exposing the rats to cigarette smoke once daily for 14 days. The rats were smoked for 90 min per day in 2 portions with a break of 10 min. 18 Marlboro cigarettes (with a tar content of 11 mg) were given each time. LPS was administered dropwise via airway at 200 μg/rat once weekly. The administration dropwise was performed on days 6 and 13 of smoke exposure (on the day of LPS administration dropwise, only LPS was administered dropwise for modeling without smoke exposure).
2. Administration: an aqueous solution of 1% DMSO/20% PEG400/79% (HP-b-CD) was used as the vehicle, and the drugs were administrated intragastrically everyday at a volume of 5 mL/kg for 2 weeks.
3. Endpoint: On day 15, pulmonary function test, sample collection, inflammatory cell count in bronchoalveolar lavage fluid, pathological analysis, and lung tissue MPO and MMP9 assay were carried out.

Procedures of Pulmonary Function Test:

After the last smoking and modeling were finished, pulmonary function was tested for each group of animals on the second day, and pulmonary resistance and compliance were detected under stimulation of methacholine chloride at different doses. The animals were anesthetized by intraperitoneal injection with 1.5 mg/kg of 25% urethane. After the animals were deeply anesthetized, airway intubation was performed by separating airways, and meanwhile, jugular veins were separated. After breathing stably, the animals were put into a plethysmograph. Drug administration pipelines were inserted into the separated jugular veins. After the animals were in rest state for 1-2 min and the breathing curves were stable, then detection was started. Rats were administered with methacholine chloride at doses of 0, 0.0083, 0.025, 0.075, 0.225, 0.675 mg/kg by jugular vein intubation. The increase in airway resistance and decrease in pulmonary compliance were observed after each administration. After 1-2 min, the parameters returned to near the baseline of the previous concentration of methacholine chloride, and methacholine chloride of the next concentration was injected. After the detection was finished, subsequent alveolar lavage and sample collection were performed.

Procedures of Euthanasia and Bronchoalveolar Lavage Fluid Collection:

After the pulmonary function test was finished, the rats were sacrificed by cervical dislocation. After the animals were confirmed dead, the lungs were carefully separated, a lavage syringe was inserted into the main trachea and fixed with 2-0 silk thread. The right lung was ligated. 5 mL of low-temperature normal saline was slowly injected through the lavage syringe. The normal saline was slowly extracted after confirming that the normal saline was injected into the left lung. The operation was repeated twice. By the three lavages, a total of 15 mL of normal saline was injected for lavage. The obtained BALF was injected into a 15 mL centrifuge tube and preserved in a storage box at 4° C. for subsequent BALF cells counting.

After BALF was collected, the right lung which was not infused was taken off and weighted. The two upper lobes of the right lung were put into a cryopreservation tube, frozen in a freezer at −80° C. for later use. Lower lobe tissues were fixed in formalin.

Procedures of Inflammatory Cell Counting and Differential Counting in Bronchoalveolar Lavage Fluid (BALF):

1 mL of homogenously mixed BALF was added into 1 mL of a solution of 1% glacial acetic acid in normal saline. Cells were counted using a hemocytometer. The remaining lavage fluid was centrifuged at 1500 r/min for 10 min at 4° C. to give a cell mass. The cells were resuspended in 200 μL of normal saline, uniformly coated on a glass slide and stained by Wright-Giemsa stain. Macrophages, neutrophils and lymphocytes in a total of 200 cells were counted under a microscope, and the proportions of the cells was calculated. For lavage fluid collection, animals failing the lavage fluid collection were not summarized.

Pathological Analysis of Lung Tissue:

Paraffin tissue blocks were prepared from formalin-fixed lung according to standard SOP of the laboratory, sliced with the thickness of 4 μm and stained by H&E. The prepared slices were sent to a pathology teaching and research room of the city institute for analysis and scoring of acute inflammatory pathological changes. Bronchiolitis is classified into scores 0-4: score 0=no inflammatory cell infiltration; score 1=mild inflammatory cell infiltration dispersed in alveoli; score 2=mediate inflammatory cell infiltration diffused in alveoli, accompanied by mild pulmonary edema; score 3=severe inflammatory cell infiltration continuously distributed, with alveolar structures eroded, local inflammatory lesions, and moderate pulmonary edema; and score 4=severe inflammatory cell infiltration diffused in alveoli, with large areas of inflammatory lesions, seriously eroded alveolar structures, and severe pulmonary edema.

Procedures of MPO and MMP9 Determination:

Frozen lung tissues were added to 1 mL of normal saline in a 2-mL EP tube, and homogenized at high speed. The homogenate and the supernatant were subjected to MPO and MMP9 assay. For the specific procedures, refer to the package insert of the kit.

Figure 36:
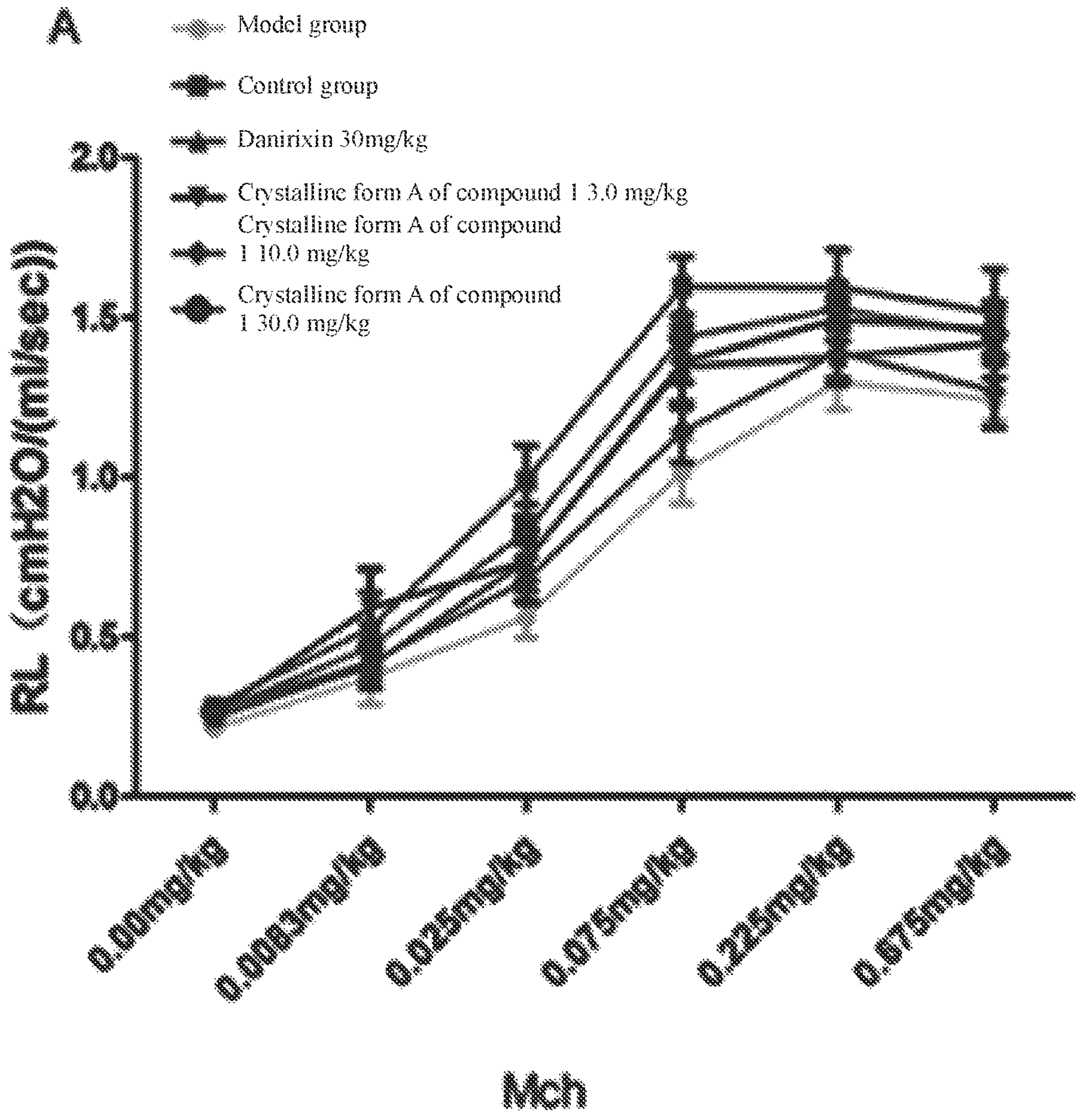
FIG. 36 shows results of methacholine-induced pulmonary function test, wherein A shows the pulmonary resistance and B shows the pulmonary compliance.
Figure 36:
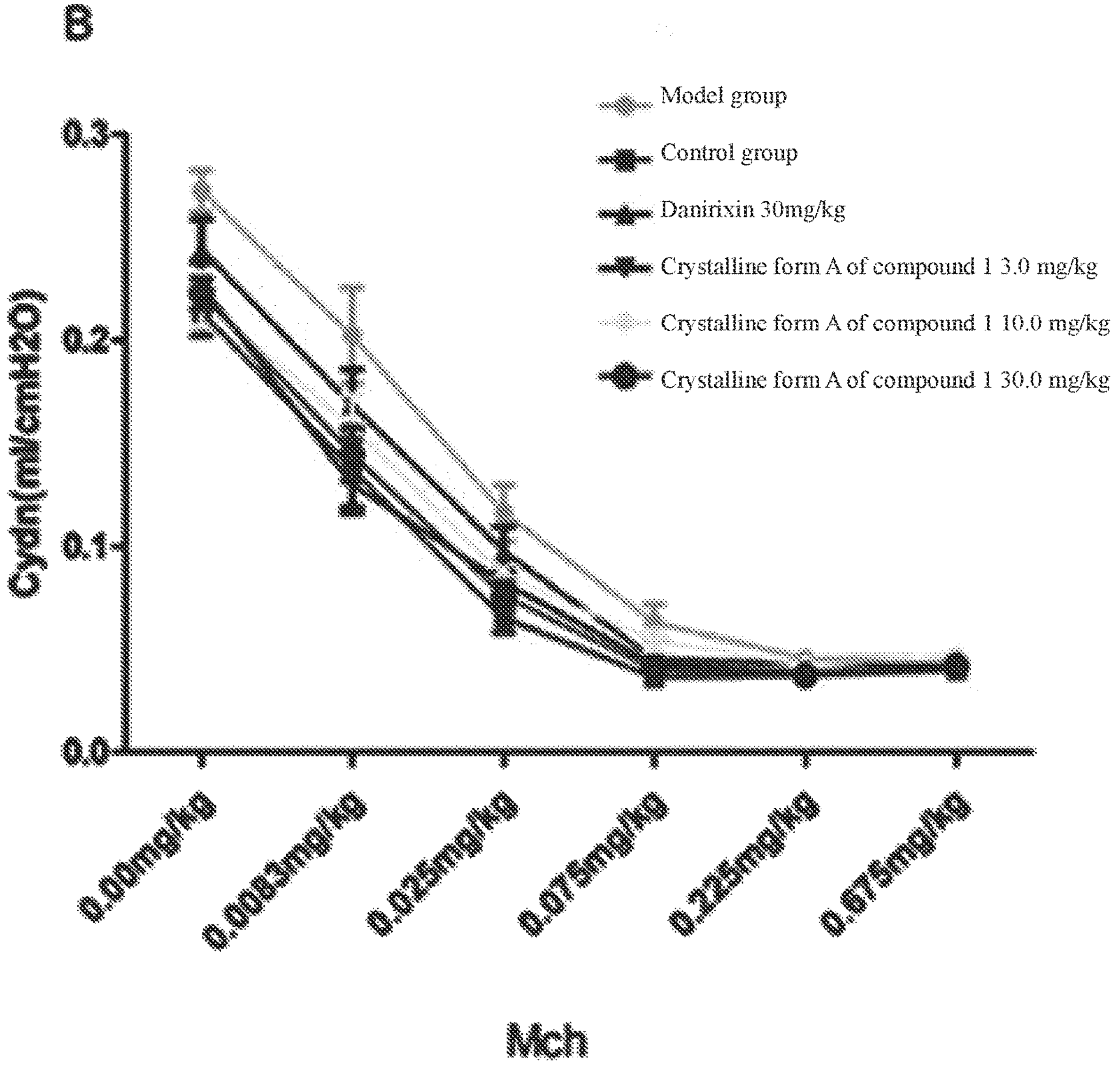

The experimental results are shown in FIGS. 36, 37, 38 and 39;

Conclusion: In the rat COPD model with acute inflammation induced by smoking+lipopolysaccharide:

1) FIG. 36 shows that in the methacholine-induced pulmonary function test, the pulmonary resistance in the model group was significantly increased and the pulmonary compliance in the model group was significantly decreased compared to those in the negative control group under the induction of methacholine at 0.025 mg/kg. The crystalline form A of compound 1 has significant effects in improving the pulmonary resistance at 3 mg/kg and 10 mg/kg, comparable to that of Danirixin at 30 mg/kg; the crystalline form A of compound 1 has significant effect in improving the pulmonary compliance at the dose of 10 mg/kg, comparable to that of Danirixin at 30 mg/kg.

Figure 37:
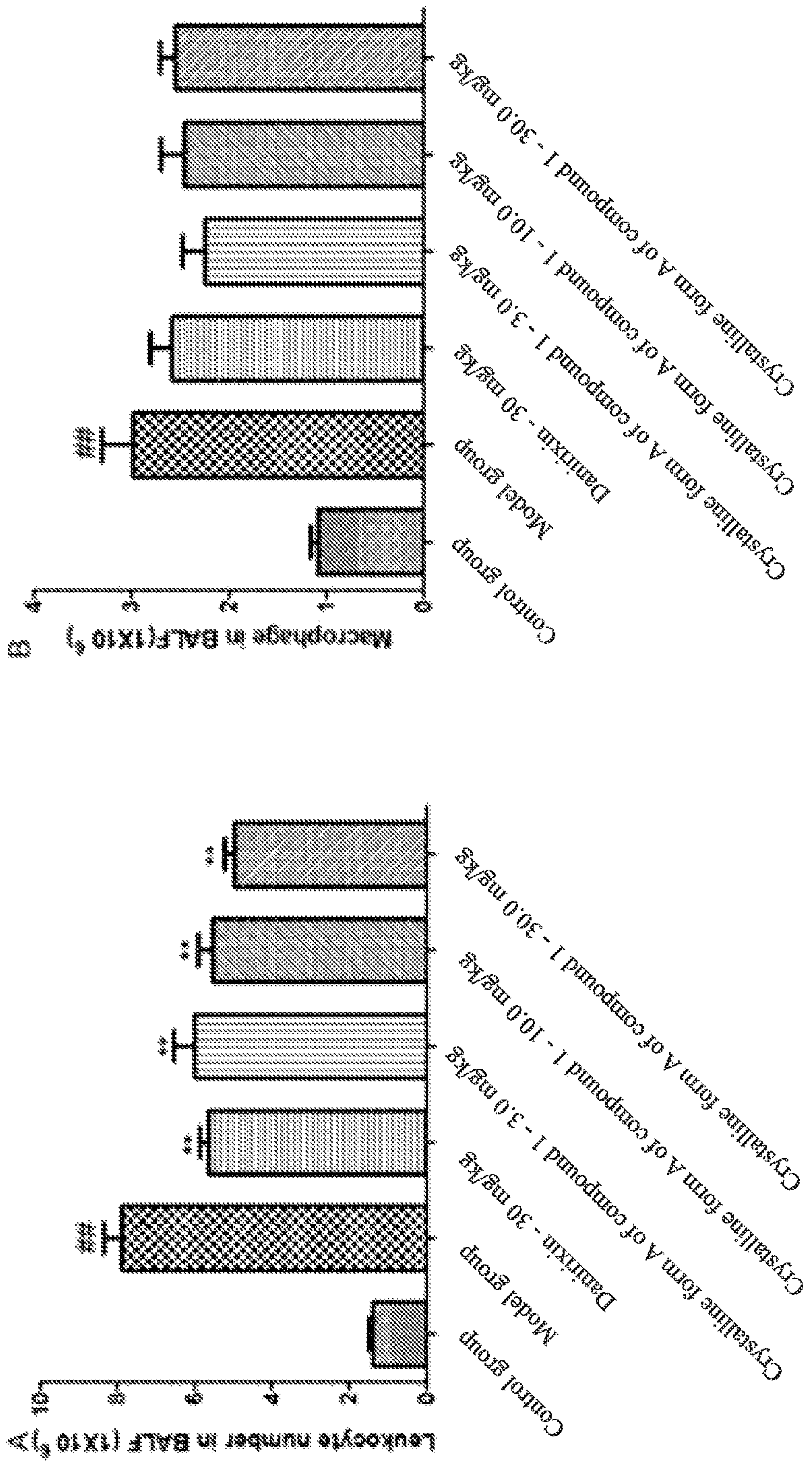
FIG. 37 shows results of various parameters in bronchoalveolar lavage fluid (BALF), wherein A shows the total leukocytes, B shows the count of macrophages, C shows the count of lymphocytes, and D shows the count of neutrophils.
Figure 37:
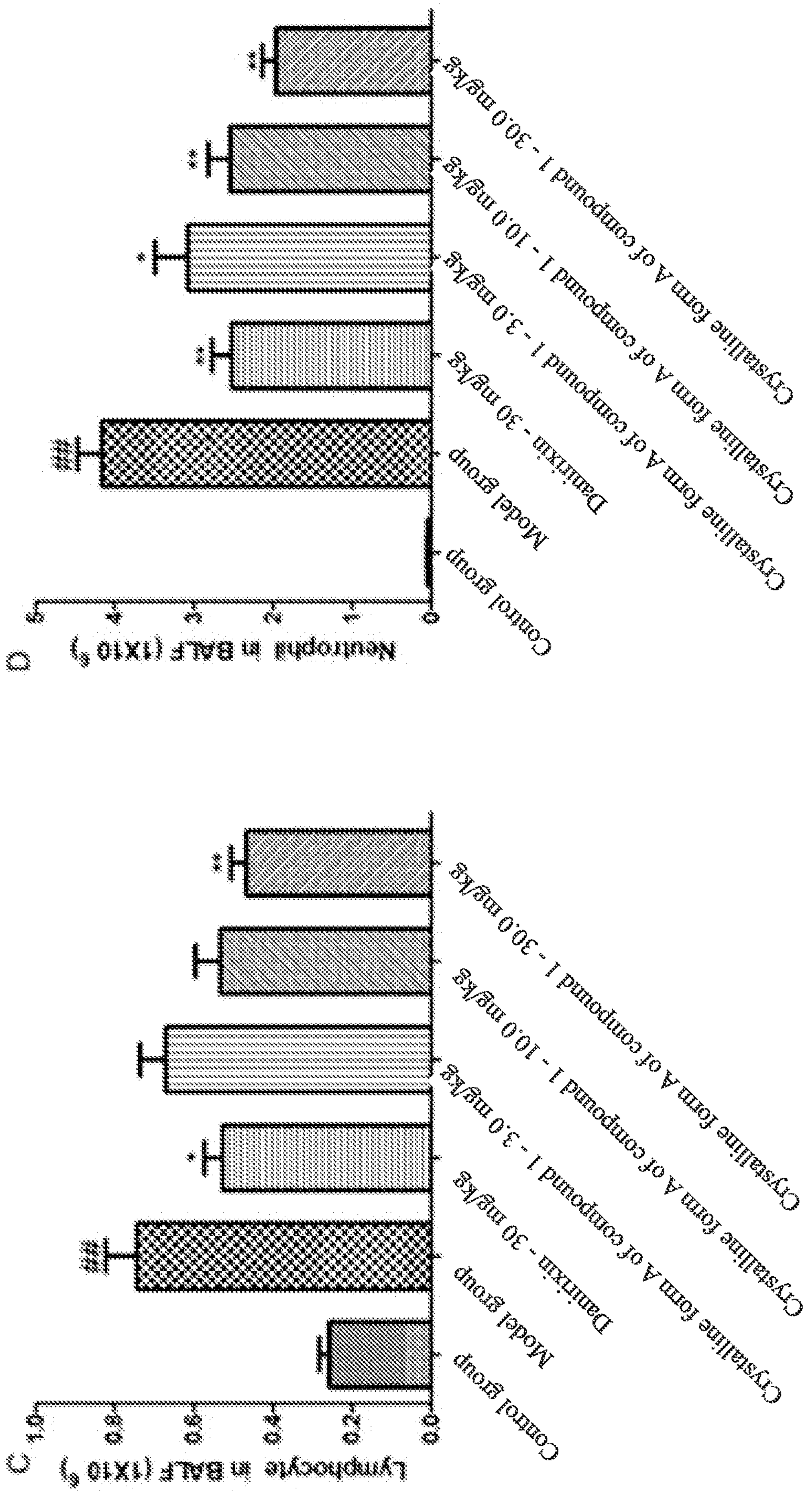

2) FIG. 37 shows that in leukocyte and neutrophil counts in bronchoalveolar lavage fluid (BALF), both leukocytes and neutrophil numbers in the model group were significantly increased compared to those in the negative control group. The crystalline form A of compound 1 can significantly reduce the number of leukocytes at various doses, with comparable effect at 10 mg/kg to that of Danirixin at 30 mg/kg. The crystalline form A of compound 1 reduced the number of neutrophils in a dose-dependent manner and shows a significant effect at down to 3 mg/kg, with comparable effect at 10 mg/kg to that of Danirixin at 30 mg/kg.

Figure 39A:
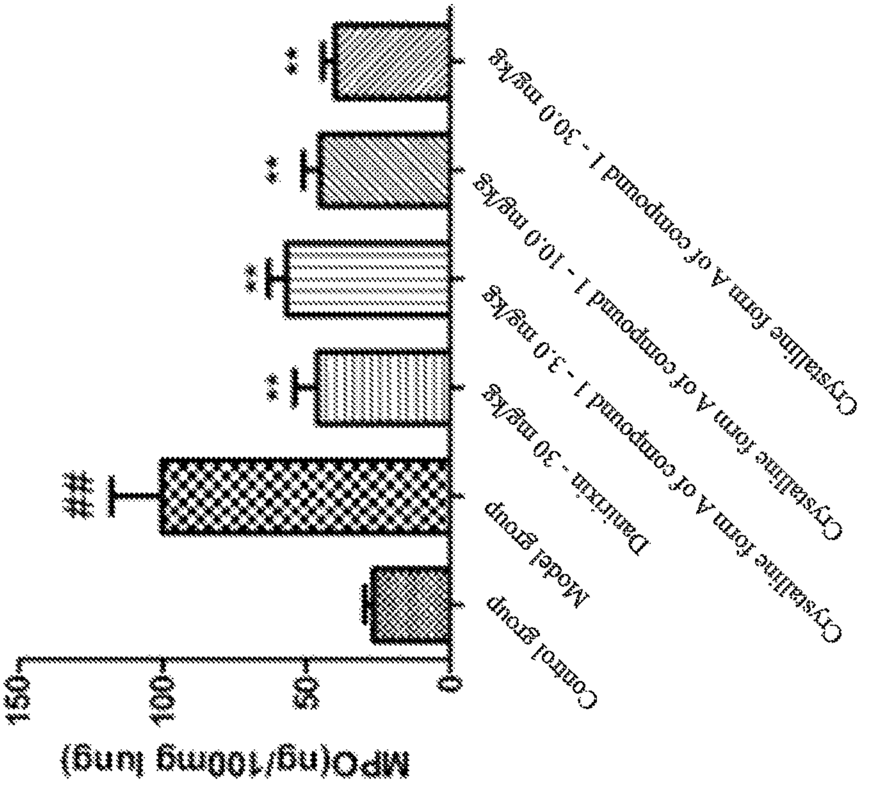
FIG. 39A shows the content assay of myeloperoxidase (MPO) in lung tissue.

3) FIG. 39A shows that in myeloperoxidase (MPO) assay in the lung tissue, the content in the model group was significantly increased compared to that in the negative control group. The crystalline form A of compound 1 can significantly reduce the MPO content in lung tissues at various doses, with comparable effect at 3 mg/kg to that of Danirixin at 30 mg/kg.

Figure 39B:
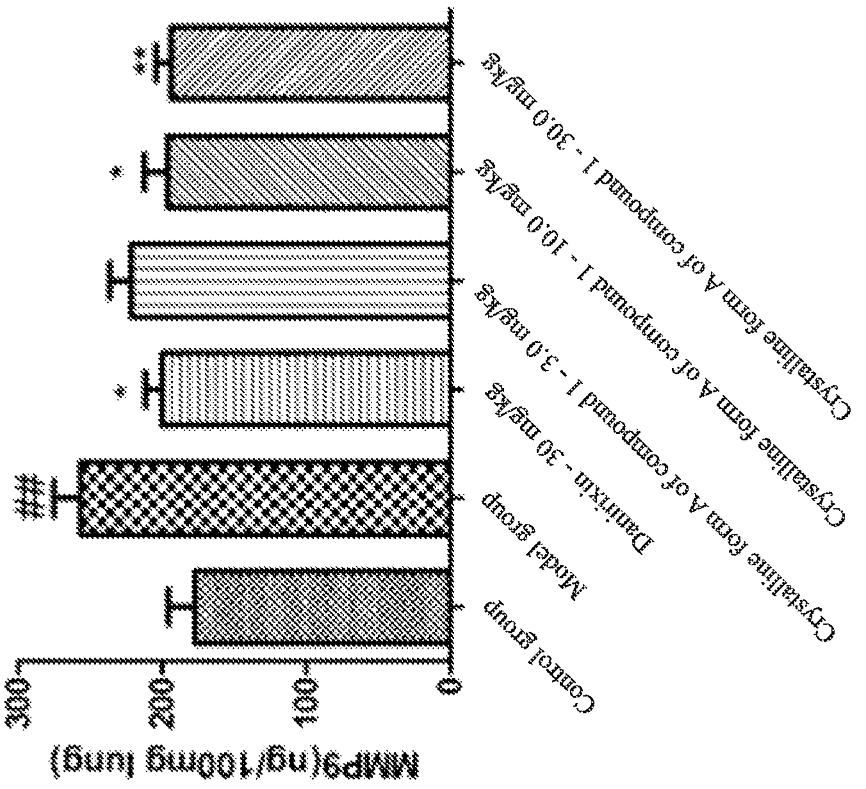
FIG. 39B shows the content assay of matrix metalloproteinase 9 (MMP9) in lung tissue.

4) FIG. 39B shows that in matrix metalloprotease 9 (MMP9) assay in the lung tissue, the content in the model group was significantly increased compared to that in the negative control group. The crystalline form A of compound 1 reduced the MMP9 content in lung tissue in a dose-dependent manner, and shows a significant effect at down to 10 mg/kg comparable of that of Danirixin at 30 mg/kg and a superior effect at 30 mg/kg to that of Danirixin at 30 mg/kg.

Figure 38:
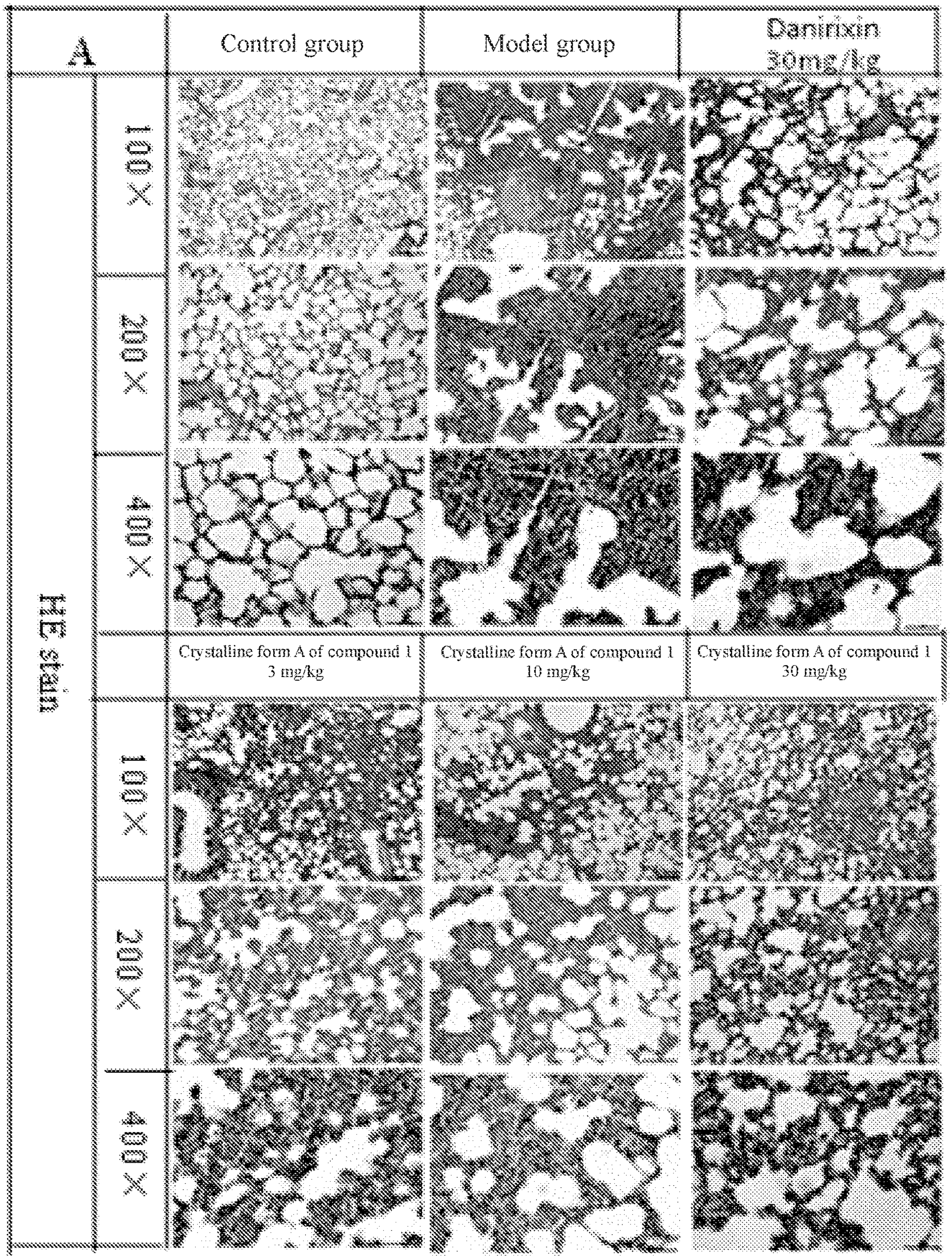
FIG. 38 shows pathological scores of the lung tissues.
Figure 38:
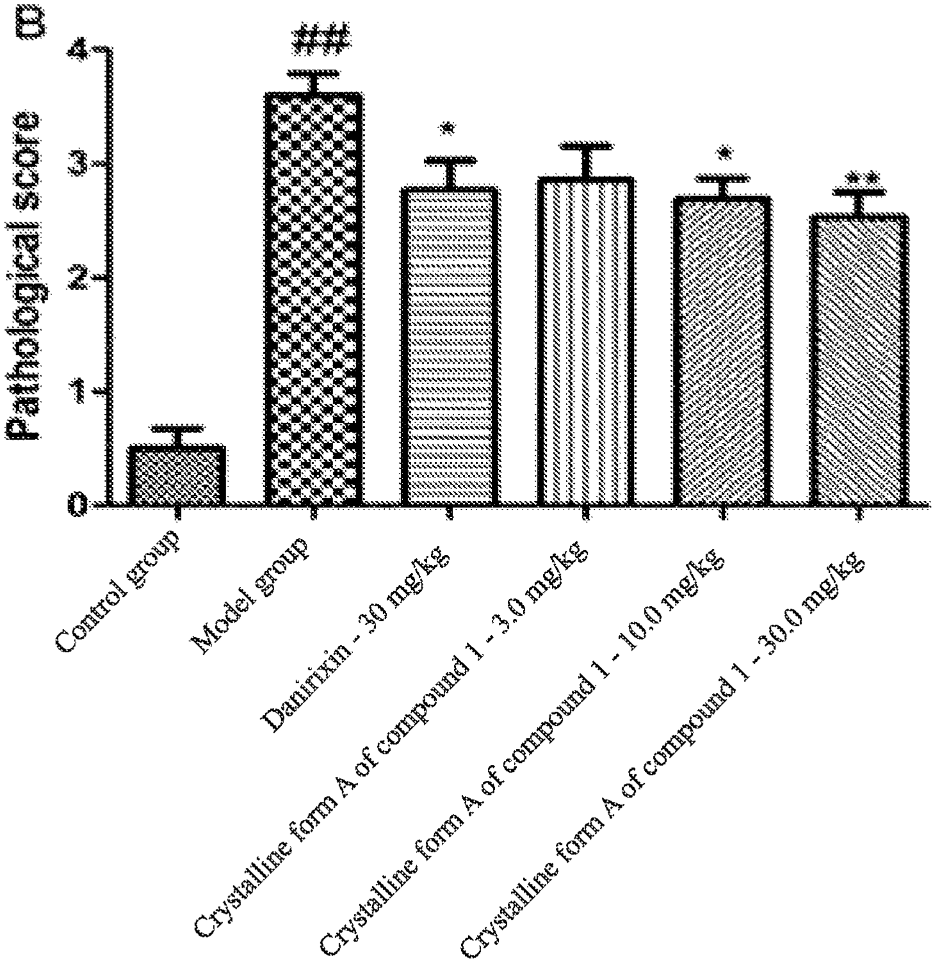

5) FIG. 38 shows that for the lung tissue pathology score, the scores in the model group were significantly increased compared to that in the negative control group. The crystalline form A of compound 1 improved the pathology score in a dose-dependent manner, and shows a significant effect at down to 10 mg/kg comparable of that of Danirixin at 30 mg/kg and a superior effect at 30 mg/kg to that of Danirixin at 30 mg/kg.

Summary: In this assay, both the crystalline form A of compound 1 and the reference drug Danirixin show significant anti-inflammatory effect, and the crystalline form A of compound 1 shows significant pulmonary function improvement and anti-inflammatory effects at dose of 3 mg/kg. Compared with Danirixin, the crystalline form A of compound 1 has equivalent pharmacodynamic effect at a lower dose and superior pharmacodynamic effect at the same dose. In conclusion, the crystalline form A of compound 1 has value for further research on efficacy against COPD.

The invention claimed is:

1. A crystalline form A of Compound 1 having an X-ray powder diffraction pattern (XRPD) comprising diffraction peaks at the following 2-theta values: 4.02±0.20°, 14.54±0.20°, 15.95±0.20°, 16.56±0.20°, 17.14±0.20°, 18.59±0.20°, 19.98±0.20°, and 20.67±0.20°, Compound 1

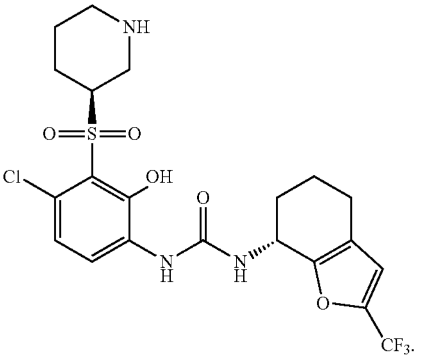

2. A method for preparing the crystalline form A of Compound 1 according to claim 1, comprising: adding the compound 1 into a solvent selected from methanol, ethanol, water, and mixtures thereof, and recrystallizing or slurrying to give the crystalline form A, Compound 1

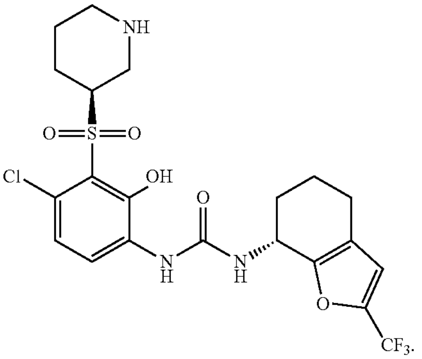

3. The method according to claim 2, wherein the solvent is methanol.

4. The method according to claim 2, wherein, in the solvent, a volume ratio of methanol, ethanol, or a combination thereof to water is 1: (0-1.5).

5. A crystalline form B of Compound 1 having an X-ray powder diffraction pattern comprising diffraction peaks at the following 2-theta values: 7.88±0.20°, 8.69±0.20°, 11.37±0.20°, 12.47±0.20°, 15.32±0.20°, 16.45±0.20°, 17.49±0.20°, and 22.90±0.20°, Compound 1
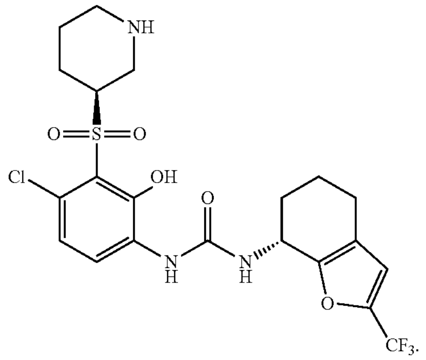
* * * * *